(12) United States Patent
Sah et al.

(10) Patent No.: US 6,835,567 B1
(45) Date of Patent: Dec. 28, 2004

(54) PNS CELL LINES AND METHODS OF USE THEREFOR

(75) Inventors: Dinah W. Y. Sah, La Jolla, CA (US); Heather K. Raymon, La Jolla, CA (US)

(73) Assignee: Signal Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/060,409

(22) Filed: Apr. 14, 1998

(51) Int. Cl.[7] .......................... C12N 5/00; C12N 5/02; C12N 5/08; C12N 15/63; C12Q 1/00

(52) U.S. Cl. .......................... 435/377; 435/4; 435/325; 435/353; 435/366; 435/368; 435/455

(58) Field of Search ................. 435/325, 353, 435/366, 368, 377, 383, 455

(56) References Cited

U.S. PATENT DOCUMENTS

| | | | |
|---|---|---|---|
| 5,580,777 A | 12/1996 | Bernard et al. | .......... 435/240.2 |
| 6,197,585 B1 | 3/2001 | Stringer | |

FOREIGN PATENT DOCUMENTS

| | | |
|---|---|---|
| GB | 2 294 945 A | 5/1996 |
| GB | 2 294 946 A | 5/1996 |
| WO | WO 89/03872 | 5/1989 |
| WO | WO 94/02593 | 2/1994 |
| WO | WO 96/14400 | 5/1996 |
| WO | WO 96/39496 | 12/1996 |
| WO | WO 97/02049 | 1/1997 |

OTHER PUBLICATIONS

A Jackowski, Neural Grafts, "Neural injury repair: hope for the future as barriers to effective CNS regeneration become clearer," British Journal of Neurosurgery, (1995) 9, pp. 303–317.*

Watson et al., Recombinant DNA, 2nd edition. pp. 413–417. (W.H. Freeman and Company, New York), 1992.*

Sah et al., "Bipotent Progenitor Cell Lines from the Human CNS," *Nature Biotechnology* 15(6): 574–580, 1997.

Anderson, "Cellular and molecular biology of neural crest cell lineage determination," *TIG* 13(7):276–280, 1997.

Arbuckle and Docherty, "Expression of tetrodotoxin–resistant sodium channels in capsaicin–sensitive dorsal root ganglion neurons of adult rats," *Neuroscience Letters* 185:70–73, 1995.

Dijkhuizen et al., "Adenoviral Vector–Directed Expression of Neurotrophin–3 in Rat Dorsal Root Ganglion Explants Results in a Robust Neurite Outgrowth Repsonse," *J. Neurobiol.* 33:172–184, 1997.

Hoshimaru et al., "Differentiation of the immortalized adult neuronal progenitor cell line HC2S2 into neurons by regulatable suppression of the v–*myc* oncogene," *Proc. Natl. Acad. Sci. USA* 93(4):1518–1523, 1996.

Kalcheim et al., "Neurotrophin 3 in mitogen for cultured neural crest cells," *Proc. Natl. Acad. Sci. USA* 89(5):1661–1665, 1992.

Mujtaba et al., "A Common Neural Progenitor for the CNS and PNS," *Developmental Biology* 200:1–15, 1998.

Nagy et al., "Cobalt Uptake Enables Identification of Capsaicin– And Bradykinin– Sensitive Subpopulations Of Rat Dorsal Root Ganglion Cells In Vitro," *Neuroscience* 56(1):241–246, 1993.

Rao and Anderson, "Immortalization and Controlled In Vitro Differentiation of Murine Multipotent Neural Crest Stem Cells," *J. Neurobiol.* 32:722–746, 1997.

Stemple and Anderson, "Isolation of a Stem Cell for Neurons and Glia from the Mammalian Neural Crest," *Cell* 71:973–985, 1992.

von Banchet et al., "Bradykinin binding sites on isolated cultured dorsal root ganglion cells demonstrated with gold–labelled bradykinin," *The Peptidergic Neuron*, Krisch et al. (eds.), Birkhäuser Verlag Basel/Switzerland, 1996, pp. 157–162.

Hales and Tyndale, "Few Cell Lines with $GABA_A$ mRNAs Have Functional Receptors," *The Journal of Neuroscience* 14(9): 5429–5436, 1994.

McQuillin et al., "Optimization of liposome mediated transfection of a neuronal cell line," *NeuroReport* 8:1481–1484, 1997.

Mugnai et al., "Multiple and alternative adhesive responses on defined subtrata of an immortalized dorsal root neuron hybrid cell line," *European Journal of Cell Biology* 46: 352–361, 1988.

Platika et al., "Neuronal traits of clonal cell lines derived by fusion of dorsal root ganglia neurons with neuroblastoma cells," *Proc. Natl. Acad. Sci. USA* 82:3499–3503, 1985.

Théveniau et al., "Expression and Release of Phosphatidylinositol Anchored Cell Surface Molecules by a Cell Line Derived From Sensory Neurons," *Journal of Cellular Biochemistry* 48: 61–72, 1992.

Wheatley et al., "Redistribution of Secretory Granule Components Precedes That of Synaptic Vesicle Proteins During Differentiation of a Neuronal Cell Line in Serum–Free Medium," *Neuroscience* 51(3): 575–582, 1992.

Wood et al., "Novel cell lines display properties of nociceptive sensory neurons," *Proc. R. Soc. Lond. B* 241 : 187–194, 1990.

\* cited by examiner

*Primary Examiner*—Anne-Marie Falk
(74) *Attorney, Agent, or Firm*—Jones Day

(57) ABSTRACT

Conditionally-immortalized PNS progenitor cell lines are provided. Such cell lines, which may be clonal, may be used to generate neurons. The cell lines and/or differentiated cells may be used for the development of therapeutic agents to prevent and treat a variety of PNS-related diseases. The cell lines and/or differentiated cells may also be used in assays and for the general study of PNS cell development, death and abnormalities.

31 Claims, 31 Drawing Sheets

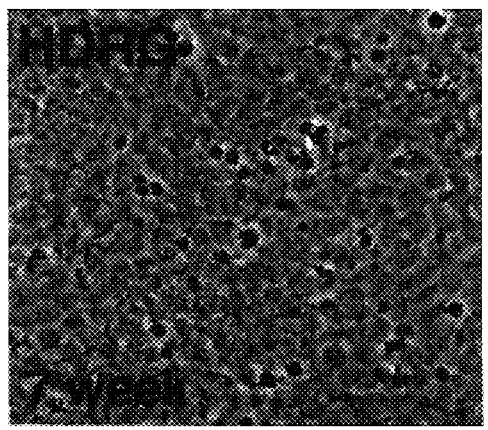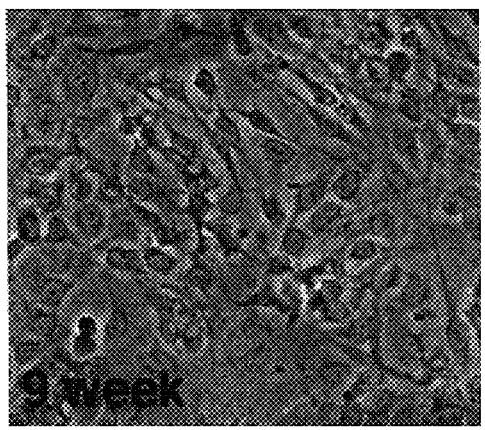
FIG.2A    FIG.2B
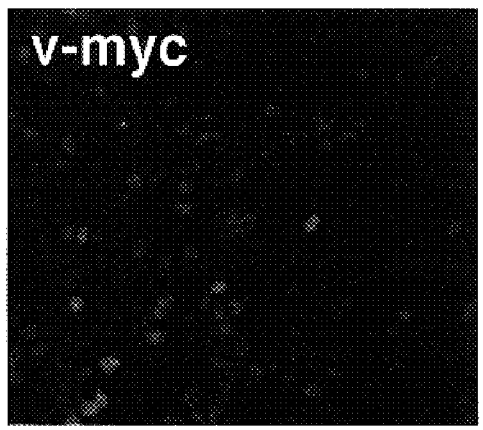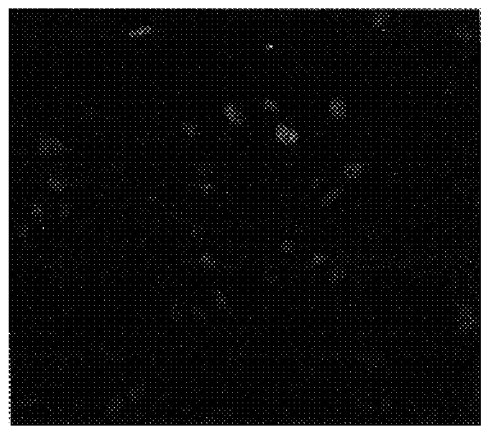
FIG.2C    FIG.2D

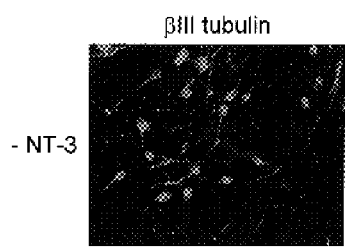 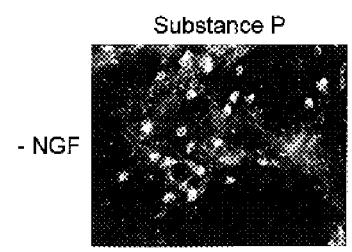 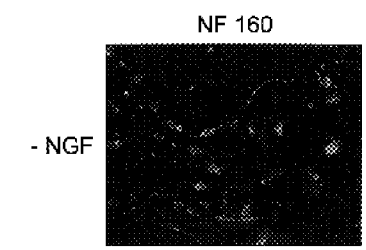
FIG.18A  FIG.18B  FIG.18C
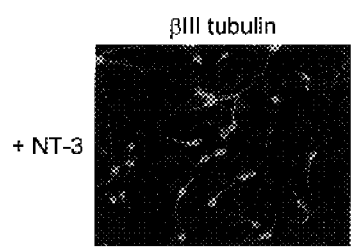 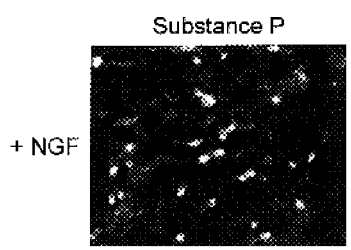 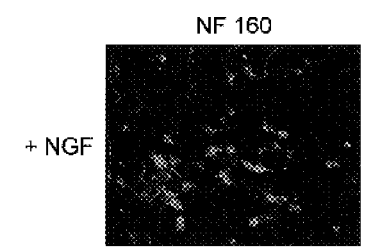
FIG.18D  FIG.18E  FIG.18F

PNS CELL LINES AND METHODS OF USE THEREFOR

TECHNICAL FIELD

The present invention relates generally to PNS cell lines. The invention is more particularly related to conditionally-immortalized neural crest stem cell lines and dorsal root ganglion progenitor cell lines, and to differentiated cells derived from such cell lines. Such cell lines and/or differentiated cells may be used in the development of therapeutic agents for the prevention and treatment of neurological diseases and other conditions. The present invention is also related to the use of such cell lines and/or differentiated cells in assays and for the study of PNS cell development, death and abnormalities.

BACKGROUND OF THE INVENTION

The peripheral nervous system (PNS), which comprises the autonomic nervous system and the sensory nervous system, can be affected by a variety of disorders that are currently difficult to treat. For example, there are no generally effective therapies for PNS disorders such as chronic pain, diabetic neuropathy, chemotherapy-induced neuropathy and Charcot-Marie Tooth, a genetic form of peripheral neuropathy. The development of therapies for PNS disorders has been considerably hampered by the lack of sufficient cells for research and development.

The molecular and cellular properties of sensory neurons have generally been studied in primary dorsal root ganglion (DRG) cultures. Such cultures contain neurons that exhibit many of the specialized features of sensory neurons. However, the limited number of cells in such cultures represents a substantial drawback for most biochemical and molecular studies, which require more material that such cultures can readily provide.

To overcome this limitation, some researchers have generated immortalized cell lines that can be differentiated into neurons exhibiting certain sensory characteristics. For example, sensory neuronal-like cell lines have been established by fusion of post-mitotic embryonic (F-11 cell line; Platika et al., *Proc. Natl. Acad. Sci. USA* 82:3499–3503, 1985) or neonatal (ND cell lines; Wood et al., *Proc. R. Soc. Lond. B* 241:187–194, 1990) rat DRG neurons with mouse N18Tg2 neuroblastoma cells. These hybrid cell lines exhibit some DRG-selective properties, including transcription factors, cytoskeletal proteins, neurotransmitters and neurotransmitter receptors. In addition, voltage-gated currents, synaptic proteins, glycosylphosphatidylinositol-linked molecules and apoptotic responses in the cells have been reported. Such properties have made these cell lines beneficial for research and drug development, but the use of these cell lines has been limited by the low percentage of cells that differentiate and by the loss of the ability to differentiate upon passaging. Furthermore, some cell lines exhibit both neural and glial characteristics, and human cells are presently unavailable.

Accordingly, there is a need in the art for stable PNS lines that can be readily differentiated. The present invention fulfills these needs and further provides other related advantages.

SUMMARY OF THE INVENTION

Briefly stated, the present invention provides conditionally-immortalized human PNS progenitor cell lines capable of differentiation into neurons. In one aspect, the present invention provides methods for producing a conditionally-immortalized rat neural crest stem cell, comprising: (a) transfecting rat neural crest cells plated on a first surface and in a first growth medium that permit proliferation with DNA encoding a selectable marker and regulatable growth-promoting gene; and (b) passaging the transfected cells onto a second surface and in a second growth medium that permit attachment and proliferation; and therefrom producing a conditionally-immortalized rat neural crest stem cell. Suitable surfaces include substrates comprising one or more of a polyamino acid, fibronectin, laminin, collagen or tissue culture plastic. Within certain embodiments, the growth-promoting gene is an oncogene such as v-myc.

Within related aspects, the present invention provides conditionally-immortalized rat neural crest stem cells capable of differentiation into neurons.

In further aspects, methods are provided for producing a conditionally-immortalized dorsal root ganglion progenitor cell, comprising: (a) transfecting dorsal root ganglion progenitor cells plated on a first surface and in a first growth medium that permit proliferation with DNA encoding a selectable marker and regulatable growth-promoting gene; and (b) passaging the transfected cells onto a second surface and in a second growth medium that permit attachment and proliferation; and therefrom producing a conditionally-immortalized dorsal root ganglion progenitor cell Within certain embodiments, the dorsal root ganglion progenitor cells are rat or human cells. Suitable surfaces include substrates comprising one or more of a polyamino acid, fibronectin, laminin, collagen or tissue culture plastic. Within certain embodiments, the growth-promoting gene is an oncogene such as v-myc.

Within related aspects, the present invention provides conditionally-immortalized dorsal root ganglion progenitor cells capable of differentiation into neurons. Within certain embodiments, the conditionally-immortalized dorsal root ganglion progenitor cells are transfected rat or human cells. Such cells may be capable of differentiation into sensory neurons and/or nociceptive sensory neurons.

Within further aspects, the present invention provides methods for producing neurons, comprising culturing a cell as described above under conditions inhibiting expression of the growth-promoting gene. Within certain embodiments, the cells are conditionally-immortalized rat or human dorsal root ganglion progenitor cells, and wherein the cells are cultured on a substrate in the presence of one or more differentiating agents.

Within related aspects, the present invention provides neurons produced as described above.

The present invention further provides methods for determining whether conditionally-immortalized dorsal root ganglion progenitor cells are capable of differentiation into neurons, comprising the step of determining the presence or absence of βIII-tubulin positive cells in the proliferative growth condition, and therefrom determining whether the cells are capable of differentiation into neurons.

Within other aspects, methods are provided for transplanting a PNS cell into a mammal, comprising administering to a mammal a cell as described above.

Within further aspects, methods are provided for treating a patient, comprising administering to a patient a cell as described above. Within certain embodiments, the patient may be afflicted with chronic pain and/or a pathological condition characterized by neurodegeneration (e.g., a neuropathy).

Methods are also provided for screening for an agent that modulates activity of a protein produced by a PNS cell, comprising; (a) contacting a cell produced as described above with a candidate agent; and (b) subsequently measuring the ability of the candidate agent to modulate activity of a protein produced by the cell.

The present invention further provides methods for detecting the presence or absence of a protein in a sample, comprising: (a) contacting a sample with a cell as described above; and (b) subsequently detecting a response in the cell, and therefrom detecting the presence of a protein in the sample.

Methods are further provided for identifying a human PNS gene or protein, comprising detecting the presence of a gene or protein within a culture of cells as described above.

Within further aspects, the present invention provides methods for screening for an agent that affects PNS cell death, comprising: (a) contacting a cell as described above with a candidate agent under conditions that, in the absence of candidate agent, result in death of the cell; and (b) subsequently measuring the ability of the candidate agent to affect the death of the cell.

The present invention further provides methods for screening for a protein that regulates PNS cell death, comprising: (a) altering the level of expression of a protein within a cell as described above; and (b) subsequently measuring the affect of the alteration on the death of the cell, and therefrom identifying a protein that regulates PNS cell death.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 2A–2D are photographs of retrovirally infected human DRG progenitor cultures prepared from 7 week (FIGS. 2A and 2C) and 9 week (FIGS. 2B and 2D) gestational age DRG cells in proliferative growth conditions. FIGS. 2A and 2B show the morphology of the cells; FIGS. 2C and 2D show the cells immunolabeled for v-myc.

FIG. 4A shows the morphology of the cells; FIGS. 4B–4D show the cells immunolabeled for β-III tubulin (FIG. 4B), NF160 (FIG. 4C) and substance P (FIG. 4D).

FIG. 6A shows clone C10 and FIG. 6B shows clone C12.

FIG. 7A is a photograph showing the morphology of the cells in proliferative conditions; FIG. 7B shows the cells in FIG. 7A immunolabeled for v-myc; FIG. 7C shows the morphology of the cells in the presence of tetracycline (1 μg/mL); and FIG. 7D shows the cells in FIG. 7C immunolabeled for v-myc. FIG. 7E is a histogram showing the percentage of v-myc positive cells in proliferative conditions and after differentiation with tetracycline (tet), as indicated.

FIG. 10 shows the morphology of the cells and FIG. 10B shows the cells immunolabeled for v-myc.

FIG. 11A shows the cells in the proliferative condition (in the absence of tetracycline); FIG. 11B show the cells in the presence of tetracycline (1 μg/mL); FIG. 11C shows the cells in the presence of tetracycline (1 μg/mL), epidermal growth factor (EGF; 100 ng/mL), basic fibroblast growth factor (FGF; 4 ng/mL) and nerve growth factor (NGF; 20 ng/mL); and FIG. 11D shows the cells in the presence of tetracycline (1 μg/mL) and leukemia inhibitory factor (LIF; 100 ng/mL).

FIG. 15A shows the cells immunolabeled for NF160 and FIG. 15B shows the morphology of the cells.

FIGS. 18A–18F are photographs illustrating the immunolabeling of β-III tubulin (FIGS. 18A and 18D), substance P (FIGS. 18B and 18E) and NF160 (FIGS. 18C and 18F) in representative conditionally-immortalized rat DRG cultures differentiated with tetracycline (1 μg/mL), rat serum (2.5%), retinoic acid (0.5 μM), NGF (100 ng/mL) and CNTF (10 ng/mL), in the presence (FIGS. 18D–18F) or absence (FIGS. 18A–18C) of NT-3 (10 ng/mL).

DETAILED DESCRIPTION OF THE INVENTION

Figure 1A:
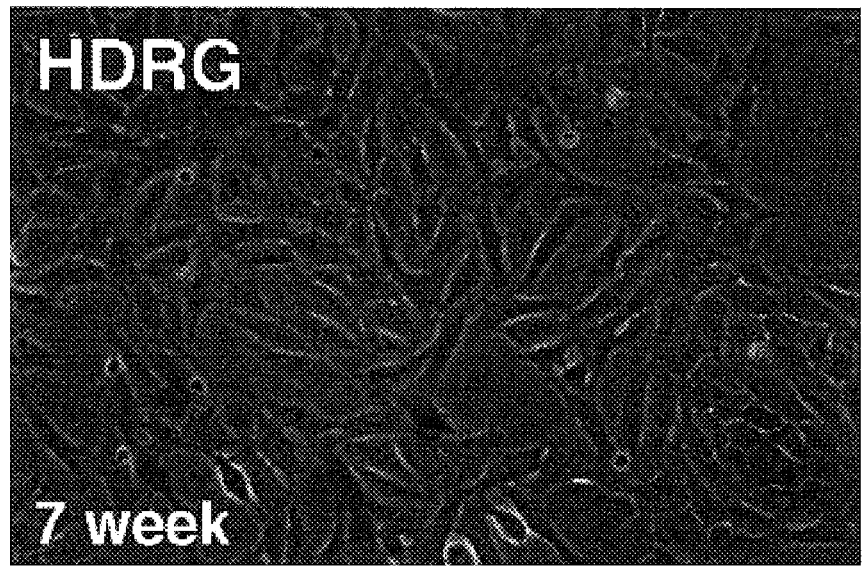
FIGS. 1A and 1B are photographs showing the morphology of retrovirally infected human DRG progenitor cultures prepared from 7 week (FIG. 1A) and 9 week (FIG. 1B) gestational age DRG cells. The cells were photographed in proliferative growth conditions.

As noted above, the present invention is generally directed to conditionally-immortalized PNS progenitor cell lines, differentiated cells generated from such cell lines and methods of using such progenitor and/or differentiated cells.

In particular, the present invention is directed to conditionally-immortalized neural crest stem cells and dorsal root ganglion progenitor cells which are capable of differentiation into neurons, and to the use of such cells for drug discovery and development, transplantation studies, therapeutic methods and a variety of assays. Conditionally-immortalized PNS progenitor cell lines of the present invention may, but need not, be clonal cell lines. The cell lines described herein provide an infinite, renewable supply of homogeneous cells and facilitate PNS drug development.

Conditionally-immortalized PNS progenitor cells may generally be prepared from any fetal or adult tissue that contains such progenitor cells. Suitable tissues will be apparent to one of ordinary skill in the art, and include neural crest, sensory ganglia, sympathetic ganglia, parasympathetic ganglia, adrenal medulla and peripheral nerve. Within certain embodiments, neural crest stem cells or dorsal root ganglion (DRG) neural precursor cells are conditionally immortalized and, preferably, the tissue is obtained from a human or rat. Fragments of the tissue are first dissociated using standard techniques to yield a single-cell suspension. The cells are then plated on a surface and in a medium that permit proliferation (i.e., at least 1% of the cells is allowed to double in a 24 hour period). Suitable surfaces include, but are not limited to, substrates comprising one or more of a polyamino acid (e.g., polylysine or polyornithine), fibronectin, laminin, collagen (e.g., rat tail collagen) or tissue culture plastic. One suitable medium is L-15C plus FGF-2 (human recombinant, 0.5–40 ng/ml), where L-15C comprises Leibovitz's L-15 medium with N2 supplement, 10% chick embryo extract, bovine serum albumin (1 mg/ml), dexamethasone (39 pg/ml), α-d-l-tocopherol (5 μg/ml), β-hydroxybutyrate (63 μg/ml), cobalt chloride (25 ng/ml), biotin (1 μg/ml), oleic acid (10 ng/ml), glycerol (3.6 mg/ml), α-melanocyte-stimulating hormone (100 ng/ml), prostaglandin E1 (10 ng/ml), triiodothyronine (67.5 ng/ml) and stable vitamin mix, containing aspartic acid (14 pg/ml), L-glutamic acid (14 μg/ml), L-proline (14 μg/ml), L-cystine (14 μg/ml), p-aminobenzoic acid (5 μg/mi), β-alanine (5 μg/ml), vitamin B-12 (0.2 μg/ml), i-inositol (9 μg/ml), choline chloride (9 μg/ml), fumaric acid (23 μg/ml), coenzyme A (37 ng/ml), d-biotin (2 ng/ml) and DL-6,8-thiotic acid (0.5 μg/ml). Cells may be plated at a density ranging from about 1.1 to $2.5 \times 10^5$ cells per 60 mm dish.

PNS progenitor cells may be conditionally immortalized by transfection of the plated cells with any suitable vector containing a growth-promoting gene (i.e., a gene encoding a protein that, under appropriate conditions, promotes growth of the transfected cell) such that the production and/or activity of the growth-promoting protein is regulatable by an external factor. In general, regulation of expression of the growth-promoting gene should be relatively tight (i.e., expression of the growth-promoting gene should generally be undetectable by immunofluorescent techniques as described herein when the promoter is repressed). In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein may be achieved by placing the growth-promoting gene under the control of an externally-regulatable promoter (i.e., a promoter whose activity may be controlled by, for example, modifying the temperature of the transfected cells or the composition of the medium in contact with the cells). One preferred method for external regulation employs a tetracycline (tet)-controlled gene expression system (see Gossen et al., *Proc. Natl. Acad. Sci. USA* 89:5547–5551, 1992; Hoshimaru et al., *Proc. Natl. Acad. Sci. USA* 93:1518–1523, 1996). In the absence of tet, a tet-controlled transactivator (tTA) within this vector strongly activates transcription from $ph_{CMV*-1}$, a minimal promoter from human cytomegalovirus fused to tet operator sequences. tTA is a fusion protein of the repressor (tetR) of the transposon-10-derived tet resistance operon of *E. coli* and the acidic domain of VP16 of herpes simplex virus. Low, non-toxic concentrations of tet (0.01–1.0 μg/mL) almost completely abolish transactivation by tTA.

In a preferred embodiment, the vector further contains a gene encoding a selectable marker (e.g., a protein that confers drug resistance). The bacterial neomycin resistance gene ($neo^R$) is one such marker that may be employed within the present invention. Cells carrying $neo^R$ may be selected by means known to those of ordinary skill in the art, such as the addition of 25–100 μg/mL G418 to the growth medium. It will be readily apparent that other markers may be employed, and appropriate selections may be readily performed by those of ordinary skill in the art.

Transfection may be achieved by any of a variety of means known to those of ordinary skill in the art including, but not limited to, retroviral infection. In general, plated cells may be transfected by infection with a suitable retrovirus (e.g., VSV-G pseudotyped LINX v-myc retrovirus, as described further below). The use of VSV-G pseudotyped retrovirus is preferred, in order to obtain higher stock concentrations of virus, to obtain stocks in the medium of choice (after centrifugation) and to increase the infectivity of human cells. Recently developed (nontraditional) VSV-G pseudotyped retroviral vectors may be especially useful for the infection of human cells, since the receptor for the VSV-glycoprotein is more abundant and less species-specific than the receptors for traditional amphotropic envelope proteins. Moreover, VSV-G pseudotyped viral particles have been reported to withstand ultracentrifugation, allowing concentration of virus and resuspension in growth medium compatible with neural progenitor cell growth (see Burns et al., *Proc. Natl. Acad. Sci. USA* 90:8033–8037, 1993).

For example, a progenitor cell culture prepared as described above may be infected within 4 days after plating by incubation for about 20 hours with retrovirus in the presence of 4 μg/mL polybrene. Retrovirus may then be removed by feeding the cultures fresh medium.

Following transfection, cultures are passaged onto a surface and in a growth medium that permit attachment and proliferation (i.e., at least 1% of the cells double in a 24 hour period). Proliferation may be assessed as described above. The ability of a surface to permit attachment may be determined using visual microscopic inspection. In general, about 20% of the cells should adhere to the surface. A suitable growth medium is as described above. Suitable surface include, but are not limited to, substrates comprising one or more of a polyamino acid (e.g., polylysine or polyornithine), fibronectin, laminin, collagen (e.g., rat tail collagen) or tissue culture plastic. Preferably, the substrate is tissue culture plastic or a surface treated with fibronectin (e.g., tissue culture plastic coated with 16–100 μg/mL fibronectin). Cultures are then fed every 2–3 days with growth medium. The conditionally-immortalized PNS progenitor cell lines may be passaged using standard techniques, such as by trypsinization, when greater than 50% confluent. Cells may also be frozen in liquid nitrogen for long-term storage.

Clonal cell lines may be isolated from a conditionally-immortalized PNS progenitor cell line prepared as described above. In general, such clonal cell lines may be isolated using standard techniques, such as by limit dilution or using cloning rings, and expanded. Clonal cell lines may generally be fed and passaged as described above.

Conditionally-immortalized human PNS progenitor cell lines (which may, but need not, be clonal) may generally be induced to differentiate into neurons by inhibiting the expression of the growth-promoting gene (i.e., suppressing the production and/or activity of the growth-promoting protein). For example, if the gene encoding the growth-promoting protein is under the control of an eternally-regulatable promoter, the conditions (e.g., temperature or composition of medium) may be modified to suppress transcription of the growth-promoting gene. For the tetracycline-controlled gene expression system discussed above, differentiation may be achieved by the addition of tetracycline to suppress transcription of the growth-promoting gene. In general, 1 $\mu$g/mL tetracycline for 4–5 days is sufficient for neuronal morphological differentiation. High cell densities are not required for differentiation.

In general, cells may be differentiated on a substrate. A preferred substrate for differentiation of rat DRG cells is a rat tail collagen substrate, although other substrates including polylysine, polyornithine, fibronectin, polyornithine/laminin or merosin may also be used. Such substrates may also be used for differentiation of immortalized rat neural crest cells. For immortalized human DRG cells, the use of polyornithine laminin is preferred, although other substrates such as rat tail collagen are also suitable.

To further promote differentiation, additional differentiating agents may be included in the growth medium. It has been found, within the context of the present invention, that improved differentiation may be achieved in growth medium containing tet (e.g., 1 $\mu$g/mL) and serum (e.g., human or rat serum; 2.5%). Other differentiating agents that may provide further benefits include retinoic acid (e.g., 0.5 $\mu$M), neurotrophin-3 (NT-3, e.g., 50 ng/mL), forskolin (e.g., 10 $\mu$M), dibutyryl cyclic AMP (e.g., 100 $\mu$M), 3-isobutyl-1-methylxanthine (IBMX; e.g., 50 $\mu$M), glial cell-derived neurotrophic factor (GDNF; e.g., 25 ng/mL), ciliary neurotrophic factor (CNTF; e.g., 25 ng/mL) and/or nerve growth factor (NGF; e.g., 20–25 ng/mL). For example, conditions particularly beneficial for differentiation of immortalized rat DRG progenitor cells include tetracycline (1 $\mu$g/mL), rat serum (2.5%), retinoic acid (0.5 $\mu$M) and NGF (20 ng/mL), plus either IL-11 or IL-1$\beta$ (10 ng/mL), in combination with a rat tail collagen substrate. As another example, conditions particularly beneficial for differentiation of immortalized human DRG progenitor cells include tetracycline (1 $\mu$g/mL), human serum (2.5%), forskolin (10 $\mu$M) and GDNF-(25 ng/mL), CTNF (25 ng/mL) plus NGF (25–50 ng/mL). The use of differentiating agents is discussed in greater detail below.

Characterization of both progenitor and differentiated cell lines may generally be performed using techniques well known to those of ordinary skill in the art, including morphological analysis of cell type, immunocytochemistry and PCR (to identify cell type-specific markers and receptors, and to confirm the presence of the growth-promoting gene) and electrophysiological analysis of voltage- and ligand-gated currents. Briefly, neuronal cells may be identified morphologically based on the presence of phase bright cell bodies and long, thin processes. Neuronal markers include MAP2a/b, tau and neurofilament. In addition, $\beta$III-tubulin may be used as an early neuronal marker, NF160 is a mature neuronal marker, and substance P and calcitonin gene related peptide (CGRP) are nociceptive markers (see Hunt and Rossi, *Philos. Trans. R. Soc. Lond. (Biol.)* 308:283–289, 1985; Holzer, *Neuroscience* 24:739–768, 1988). The presence or absence of such markers may be readily determined using standard immunofluorescence techniques (employing, for example, commercially available primary antibodies and fluorescent reagents) and the levels of mRNA encoding such markers may be determined using PCR or hybridization techniques. Electrophysiological analyses familiar to those of ordinary skill in the art may be employed to evaluate the sodium, potassium and calcium currents, as well as ligand-gated currents (e.g., ATP and capsaicin), therefrom determining the levels of functional channels and receptors.

As noted above, conditionally immortalized PNS progenitor cells as described herein are capable of differentiation into neurons. The percentage of cells differentiating into neurons, as well as the integration site (e.g., v-myc), is generally stable through more than 65 generations. Certain conditionally immortalized PNS progenitor cells can differentiate into nociceptive sensory neurons (i.e., the subset of sensory neurons that mediate pain sensation). Nociceptive sensory neurons may be identified based on the expression of nociceptive markers, including capsaicin sensitivity, substance P and CGRP. A renewable source of nociceptive sensory neurons, such as a cell line that can be differentiated into nociceptive sensory neurons, is particularly useful for basic research and drug discovery for pin including, but not limited to, novel gene discovery, target (gene or protein) validation and in vitro assays and screens.

In certain aspects of the present invention, conditionally-immortalized PNS progenitor cell lines may be used in a variety of in vitro assays and screens. In one such aspect, the cell lines may be used in in vitro assays for agents that inhibit the capsaicin response. Briefly, a clonal neuronal cell line may be differentiated under conditions in which capsaicin responsiveness can be assessed with a cobalt histological method. Capsaicin can be added to the culture in the presence or absence of a candidate agent, and cobalt uptake evaluated. Agents that block cobalt staining may act as capsaicin receptor antagonists.

Regardless of the particular model, the cells may be used to study the mechanisms of apoptosis, as well as the effect of various conditions and agents on the apoptosis of neuronal cells, using experimental techniques well known to those of ordinary skill in the art. For example, the cells may be used to screen for an agent that affects PNS cell death. Such a screen may be performed by contacting the cells during growth factor withdrawal with a candidate agent and then evaluating the ability of the candidate agent to affect the subsequent level of apoptosis. Similarly, the cells may be used to screen for a protein that regulates PNS cell death. In such a screen, the level of expression or activity of a candidate protein (e.g., an enzyme) is altered within the cells (using standard techniques) and then the affect of the alteration on the level of apoptosis following treatments (including, but not limited to, growth factor withdrawal) is measured.

In another aspect of the present invention, the cell lines described herein may be used within a system for studying protein and/or gene expression in a PNS cell environment. For example, receptor expression and/or activity may be assayed, and the effect of various modifications on such expression and/or activity may be evaluated, using methods well known to those of ordinary skill in the art. In one such method, cell lines may be permanently or transiently transfected with one or more genes of interest such as, but not limited to, genes that produce or modify membrane proteins, secreted proteins or intracellular proteins of interest. Such genes include ion channels, neurotransmitter receptors and/or MAP kinases. Within this and other aspects described herein, conditionally-immortalized PNS progenitor cells may be employed without differentiation, or differentiated cells may be used. In addition, cells of varying ages and grown in any of a variety of conditions may be employed. The cell lines of the present invention have many advantages over existing cell lines for such studies, including the ability to provide clonal cell lines capable of producing neurons, and the property of conditional-immortalization, which allows arrest at specific stages of development. The selection of particular cells for any given study will depend on the goals of the study, and those of ordinary skill in the art will be readily able to prepare appropriate PNS cells using the techniques described herein.

In yet another aspect, the differentiated or undifferentiated conditionally-immortalized PNS cell lines described herein may be used in any of a variety of nucleic acid and/or protein assays. To detect a particular nucleic acid sequence (i.e., DNA and/or RNA) within such PNS cells, the well known methods of PCR and various hybridization techniques may be employed. Such assays may be readily designed and performed using methods described, for example, in Sambrook et al., *Molecular Cloning: A Laboratory Manual*, Cold Spring Harbor Laboratories, Cold Spring Harbor, N.Y., 1989. To detect a protein, the detection reagent is typically an antibody, which may be prepared as described below. There are a variety of assay formats known to those of ordinary skill in the art for using an antibody to detect a protein in a sample. See, e.g., Harlow and Lane, *Antibodies: A Laboratory Manual*, Cold Spring Harbor Laboratory, 1988. Antibodies for use in such assays may be polyclonal or monoclonal. Antibodies may be prepared by any of a variety of techniques known to those of ordinary skill in the art and monoclonal antibodies specific for a protein of interest may be prepared, for example, using the technique of Kohler and Milstein, *Eur. J. Immunol.* 6:51 1–519, 1976, and improvements thereto.

In a related aspect, the differentiated or undifferentiated conditionally-immortalized PNS cell lines described herein may be used in any of a variety of screens for agents that modulate the activity of a protein produced by a PNS cell. Modulation includes the suppression or enhancement of the activity of the protein of interest. Such modulation may occur at the transcriptional or translational level, or may be the result of altering the activity of the intact protein. Modulation of protein activity may be direct (i.e., the modulating agent may interact directly with the protein of interest) or may be indirect (i.e., the modulating agent may alter the expression and/or activity of one or more other proteins which in turn modulate the activity of the protein of interest). Modulating agents may be antibodies (e.g., monoclonal), polynucleotides or other drugs. Agents that modulate the activity of any cellular protein may be identified within such screens. In particular, modulating agents may be identified for proteins such as neurotransmitter receptors (e.g., ATP receptors, capsaicin receptors), growth factor receptors (e.g., receptors for FGF-2, NGF, BDNF, NT-3, GDNF and/or CTNF) or ion channels (e.g., sodium channels, calcium channels and/or potassium channels).

In general, modulating agents may be identified by contacting a PNS cell as described herein with a candidate agent, and evaluating the effect of the candidate agent on the level or activity of the protein of interest using standard techniques, such as PCR or hybridization (for evaluating levels of mRNA) or any of a variety of immunoassays or functional assays appropriate for the protein of interest. For example, calcium-sensitive or voltage-sensitive dye coupled assays, cAMP measurements and/or receptor binding assays may be employed to evaluate the effect of a candidate modulating agent. In general, a suitable amount of antibody or other agent for use in such a screen will vary depending on the particular protein, but will range from about 10 µg to about 100 mg.

In a further aspect, the PNS progenitor cell lines described herein may be used in the identification of novel genes and proteins present in human PNS cells. Conventional or newer techniques, such as PCR, differential display, hybridization, expression library screens, immunoassays and two-hybrid screens may be employed for such identification. A particularly useful technique is differential gene screening. Clonal PNS cell lines as described herein are particularly suited to such studies because they are derived from a single parental cell and, therefore, PNS cell-specific genes are amplified with respect to non-clonal cell lines. Novel genes and proteins that are expressed upon experimental manipulation (e.g., sensory neuronal differentiation or induction of apoptosis) may also be identified.

Conditionally-immortalized PNS progenitor cell lines of the present invention may also be used in assays to detect the presence or absence of a particular protein in a sample. In general, an assay may be performed by contacting PNS progenitor cells with a sample and then measuring a response induced by the protein within the cells using methods familiar to those of ordinary skill in the art. For example, a response may be measured using differential display techniques.

In other aspects, the PNS progenitor cell lines described herein may be used in vivo, in transplantation studies and for treatment of a patient. For example, cells may be transplanted by grafting into the nervous system of animals such as rats, mice or monkeys. Studies may address the differentiation of the cells when transplanted into the developing or adult PNS. The ability of the cells to serve as therapeutic agents in pathological conditions can also be examined. In particular, the cells themselves may have the capacity to functionally replace neurons that die in neurodegenerative disorders or may serve as sources of agents (such as trophic factors) that have therapeutic benefit. Such agents may be produced by endogenous genes or by genes transfected into the cells.

For treatment of a patient, conditionally-immortalized human PNS progenitor cells and/or modulating agents (as described above) may be administered to a patient (either prophylactically or for treatment of an existing disease). Diseases that may be prevented and/or treated using PNS progenitor cells and/or modulating agents include, but are not limited to, chronic pain and pathological conditions characterized by neurodegeneration, such as neuropathies (e.g., diabetic neuropathy and chemotherapy-induced neuropathy). Cells may be transplanted by, for example, injection. Modulating agents may be administered by any of a variety of routes known to those of ordinary skill in the art. Such agents may be administered in their active form, as prodrugs (i.e., compounds that are converted to the active form within the patient) or as nucleic acid sequences encoding the modulating agent or prodrug. PNS progenitor cells for use in this aspect of the present invention may, but need not, be further transfected such that they express one or more additional proteins (such as modulating agents) within the patient.

For administration to a patient, one or more PNS progenitor cells (and/or modulating agents) are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. The selection of a carrier will depend, in part, on the nature of the substance (i.e., cells or chemical compounds) being administered. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Routes and frequency of administration, as well as doses, will vary from patient to patient and on the nature of the substance being administered. In general, the pharmaceutical compositions may be administered intravenously, intramuscularly, subcutaneously or intracavity. Doses are preferably administered daily. A suitable dose is an amount that is sufficient to show improvement in the symptoms of a patient afflicted with a disease of the PNS or to inhibit the onset of such a disease. Such improvement may be detected based on improvement and/or delay in clinical symptoms associated with the disease. In general, the amount of modulating agent present in a dose, or produced in situ by DNA present in a dose, ranges from about 1 mg to about 200 mg per kg of host. Suitable dose sizes will vary with the size of the patient, but will typically range from about 0.1 mL to about 5 mL for 10–60 kg animal.

The following Examples are offered by way of illustration and not by way of limitation.

EXAMPLES

Example 1

Retroviral Optimization for Immortalization of PNS Cell Lines

This Example illustrates the optimization of efficiency of retroviral infection of human PNS progenitor cells.

HEK293 cells (ATCC Accession No. CRL 1573) cultured in DMEM, 10% fetal bovine serum plus pen-strep (100 units/mL penicillin G plus 100 µg/mL streptomycin sulfate) were transiently co-transfected, using the calcium phosphate system (Promega ProFection kit, Promega, Madison, Wis.) with pMD.G (Naldini et al., Science 272:263–267, 1996; Naldini et al., Proc. Natl. Acad. Sci. USA 93:11382–11388, 1996) (VSV-G expression), pBS.CMV.gag.pol (within a Bluescript KS+ backbone, the immediate early CMV promoter is used to express gag/pol from Moloney Leukemia Virus, followed by a bovine polyA sequence) and LINX v-myc (tetracycline-regulatable v-myc; see Hoshimaru et al., Proc. Nail. Acad. Sci. USA 93:1518–1523, 1996) simultaneously. After approximately 16 hours, the supernatant from the culture was collected and filtered through a 0.45 µm filter. This filtrate was then centrifuged for 90 minutes at 17,500 rpm at 4° C., and resuspended in ~1/100 of the original volume. Viral stock aliquots were frozen at –80° C. The absence of viable HEK cells in the viral stocks was confirmed, as was the absence of helper virus. It was found that pseudotyped viral stocks could be reproducibly concentrated to titers of ~$10^5$/ml, resuspended in the medium of choice and stored as frozen stocks:.

VSV-G pseudotyped retroviruses were found to infect human DRG cells far more efficiently than amphotropic retroviruses. Cultures of human fetal DRG cells infected with VSV-G pseudotyped retroviruses yielded successfully infected (G418-resistant) cells, whereas sister cultures of human DRG cells infected with amphotropic retroviruses did not.

Example 2

Human PNS Cell Line Development

This Example illustrates the conditional immortalization of human DRG neural precursors.

Human fetal DRG cultures were retrovirally infected with VSV-G pseudotyped LINX v-myc, the tetracycline-regulatable v-myc oncogene. A number of putative clones were isolated by limiting dilution. Specifically, DRGs were dissociated with 1 mg/ml collagenase plus 3.6 mg/ml dispase for 20 to 40 minutes at 37° C., with mechanical trituration every 10 minutes. In one case, DNAse (0.1 mg/ml) was included during the last trituration set. The dissociated cells were plated in L-15C (see below for components), EGF-2 (40 ng/ml) plus pen-strep (5.0 units/mL penicillin G plus 50 µg/mL streptomycin sulfate) onto fibronectin-coated tissue culture plastic at a density of 1.1–2.5×$10^5$ cells per 60 mm dish. Cultures were infected for 19 hours with 50–100 µL of VSV-G pseudotyped LINX v-myc retrovirus in the presence of 4 µg/ml polybrene. The retrovirus was then removed by feeding the cultures with 4 ml of fresh medium containing pen-strep. G418 (25 to 100 µg/ml) selection was carried out for at least 2 weeks. Cloning by limiting dilution was then initiated. During the initial phases of cloning, 10% filtered conditioned medium from a parental immortalized sister culture was included in the feeding medium. Cultures were fed every 2–3 days throughout with L-15C plus FGF-2 (0.5–40 ng/ml). L-15C consists of Leibovitz's L-15 medium with N2 supplement, 10% chick embryo extract, bovine serum albumin (1 mg/ml), dexamethasone (39 µg/ml), α-d-1-tocopherol (5 µg/ml), β-hydroxybutyrate (63 µg/ml), cobalt chloride (25 ng/ml), biotin (1 µg/ml), oleic acid (10 ng/ml), glycerol (3.6 mg/ml), α-melanocyte-stimulating hormone (100 ng/ml), prostaglandin E1 (10 ng/ml), triiodothyronine (67.5 ng/ml) and stable vitamin mix, containing aspartic acid (14 µg/ml), L-glutamic acid (14 µg/ml), L-proline (14 µg/ml), L-cystine (14 µg/ml), p-aminobenzoic acid (5 µg/ml), β-alanine (5 µg/ml), vitamin B-12 (0.2 µg/ml), i-inositol (9 µg/ml), choline chloride (9 µg/ml), fumaric acid (23 µg/ml), coenzyme A (37 ng/ml), d-biotin (2 ng/ml) and DL-6,8-thiotic acid (0.5 µg/ml). The substrate used throughout for expansion of proliferating cells was fibronectin (16–100 µg/ml)—coated tissue culture plastic. Both parental cultures and clones were passaged with trypsin as necessary, typically when cultures were >50% confluent.

TABLE 1

Summary of Human DRG Immortalizations

| Plating | Gestational Age | LINX v-myc | # Putative Clones Isolated | # Distinct and Confirmed Clones[a] |
|---|---|---|---|---|
| HDRGVIII | 7 wks | pseudo. | 26 | 9 |
| HDRGIX | 9 wks | pseudo. | 6 | 1 |

[a]clonality confirmed by genomic Southern

Figure 1B:
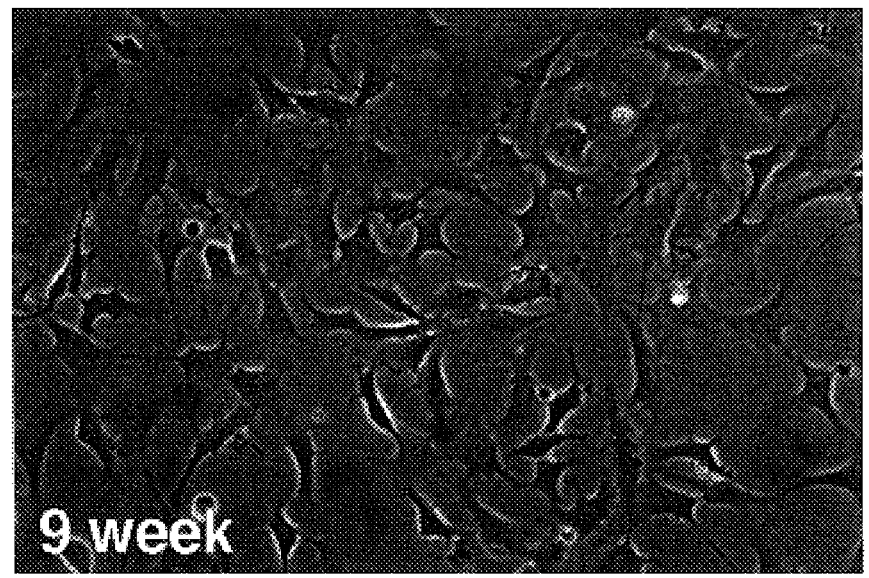
Figure 3A:
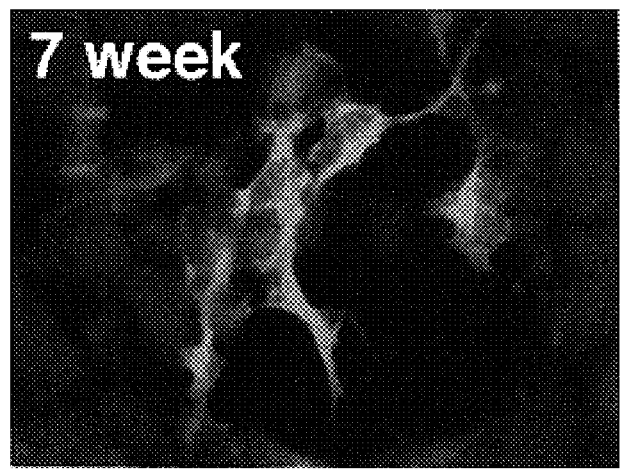
FIGS. 3A and 3B are photographs showing retrovirally infected human DRG progenitor cultures prepared from 7 week (FIG. 3A) and 9 week (FIG. 3B) gestational age DRG cells in proliferative growth conditions, where the cells are immunolabeled for β-III tubulin.
Figure 3B:
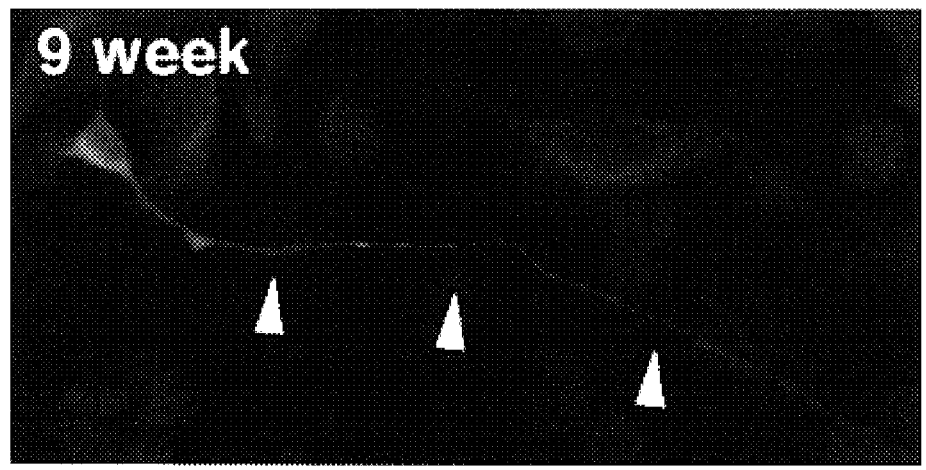
Figure 4A:
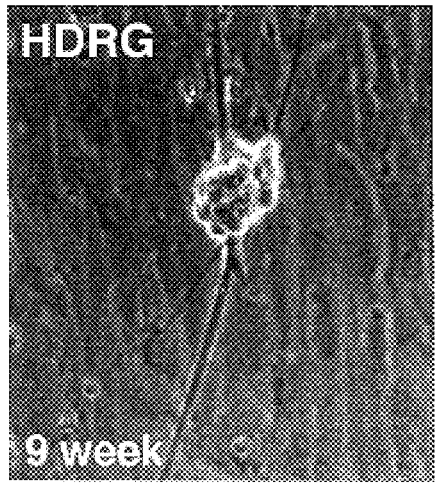
FIGS. 4A–4D are photographs of differentiated conditionally-immortalized human DRG cells prepared from 9 week gestational age DRG cells.
Figure 4B:
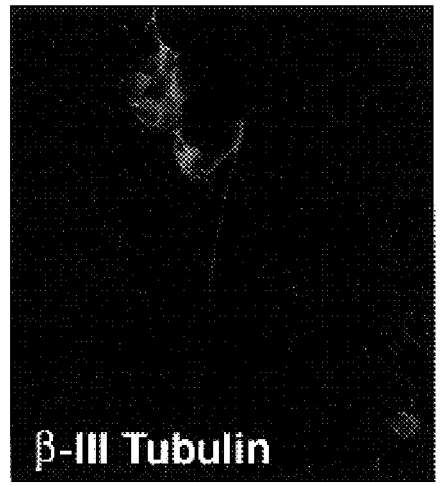
Figure 4C:
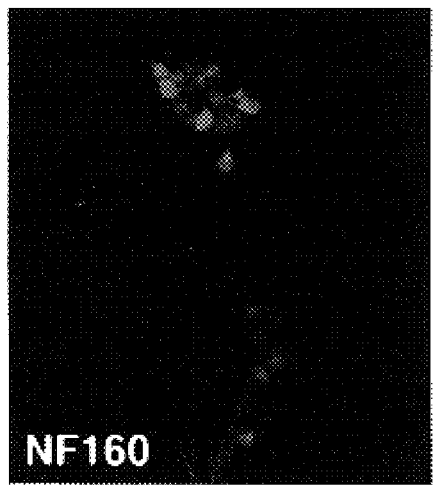
Figure 4D:
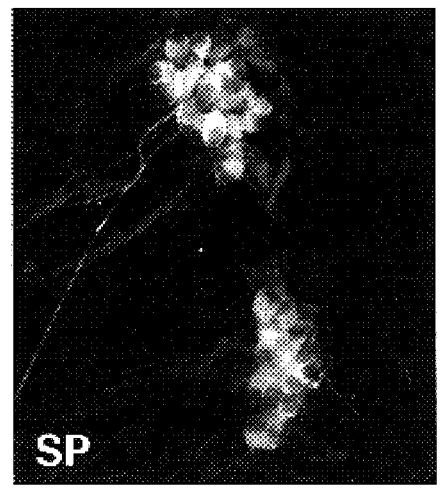

Characterization of retrovirally infected human DRG progenitor cultures. Immortalized cultures of 7 and 9 week gestational age DRG cells (HDRGVIII and HDRGIX, respectively) contained neuronal precursors. In proliferative growth conditions (FIG. 1), the morphology of G418-resistant cells resembled the morphology of rat neural crest stem cells. As expected, both parental cell cultures expressed the v-myc oncoprotein in proliferative growth conditions (FIG. 2). Moreover, in proliferative conditions, a few of the cells in both cultures expressed βIII tubulin, suggesting the presence of immortalized neuronal precursor cells (FIG. 3).

Differentiation experiments with the parental cells from HDRGVIII and HDRGIX established that immortalized cells give rise to neurons upon differentiation. The initial differentiation conditions were based on data obtained from the immortalized rat DRG cultures. Both parental human DRG cultures were differentiated for 1–1.5 weeks with tetracycline (T; 1 μg/mL), human serum (HS; 2.5%), retinoic acid (RA; 0.5 μM), GDNF (G; 25 ng/mL), CNTF (C; 25 ng/mL) and NGF (N; 25 ng/mL), or T, HS, forskolin (Fsk, 10 μM) and G, C plus N. In either treatment condition, phase-bright, process bearing cells could be observed in both HDRGVIII and HDRGIX (FIG. 4). As shown in FIG. 4, these cells stained positively for βIII tubulin, NF160 and substance P (SP). A low level of CGRP staining was observed in cells with neuronal morphology from HDRGIX. Quantitation of NF160 positive cells from HDRGIX differentiated with T, HS, RA and G, C plus N indicated that 6.8±1.9% of the cells were neurons compared to 0.7±0.4% of the cells in the proliferative condition. These data indicate that conditionally immortalized neuronal precursor cells derived from DRG can be differentiated into human peripheral neurons.

Isolation and expansion of clonal cell lines. Cloning of HDRGVIII and HDRGIX was carried out by limiting dilution. 26 and 6 putative clones were expanded from HDRGVIII (7 weeks gestational age) and HDRGIX (9 weeks gestational age), respectively.

Figure 5:
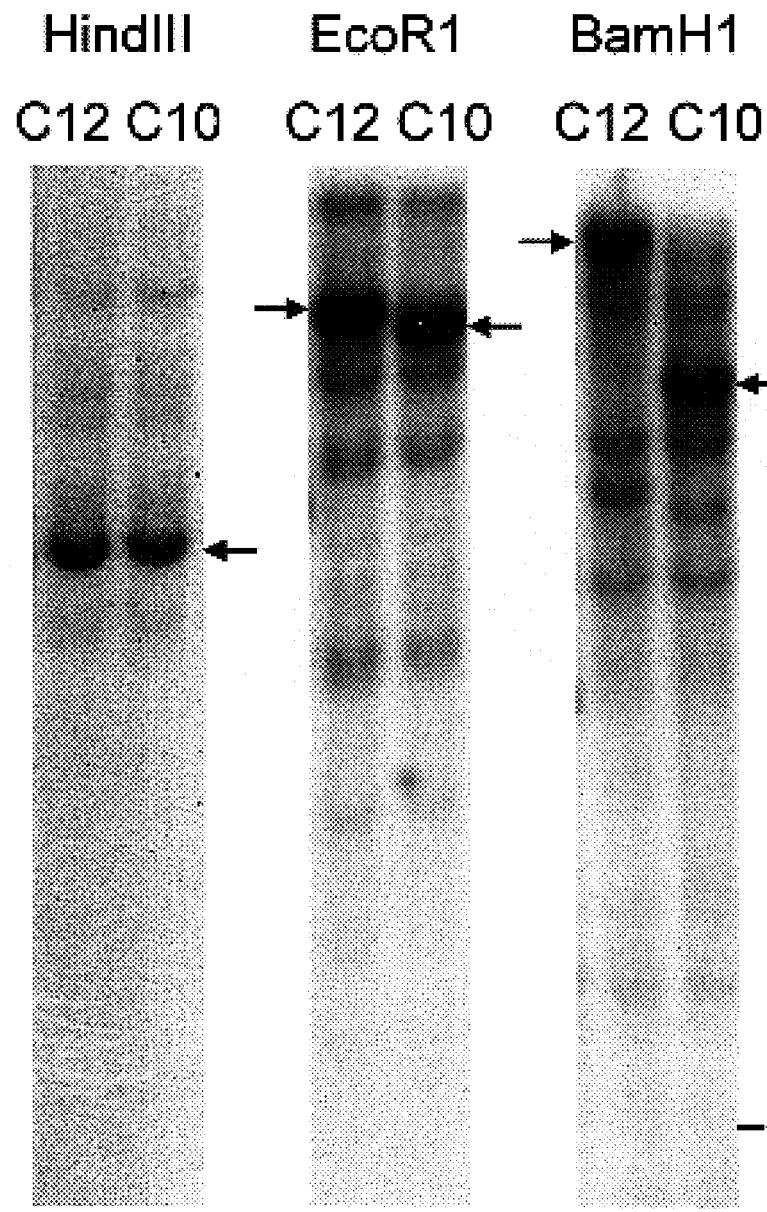
FIG. 5 is a photograph depicting the results of genomic Southern analyses of two clonal human PNS cell lines (C12 and C10, as indicated). The DNA was digested with HindIII (left two lanes), EcoRI (middle two lanes) or BamHI (right two lanes).

Genomic Southern analysis. To establish that the cell lines arose from independent integration events and were clonal, genomic Southerns were carried out. Genomic DNA was prepared from the putative clones, and digested with the restriction enzymes BamHI, EcoRI or HindIII. The resultant DNA fragments were separated on an agarose gel, transferred to nylon membranes, and probed with $^{32}$P-v-myc. HindIII cuts within the provirus near the LTRs produced unit length DNA fragments of 4.8 kb for all but one of the putative clones, as expected. Analysis of BamHI and EcoRI restriction digests of DNA from the putative clones indicated that there were a minimum of 10 clonal and distinct human PNS cell lines, including HDRGVIII-C10 and HDRGVIII-C12 (FIG. 5).

Figure 6A:
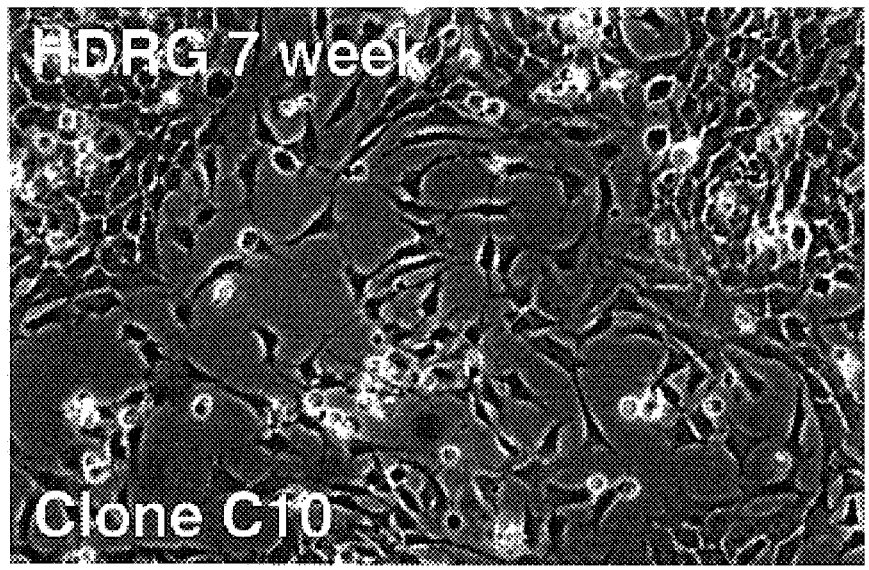
FIGS. 6A and 6B are photographs showing the morphology of two clonal human DRG progenitor cell lines.
Figure 6B:
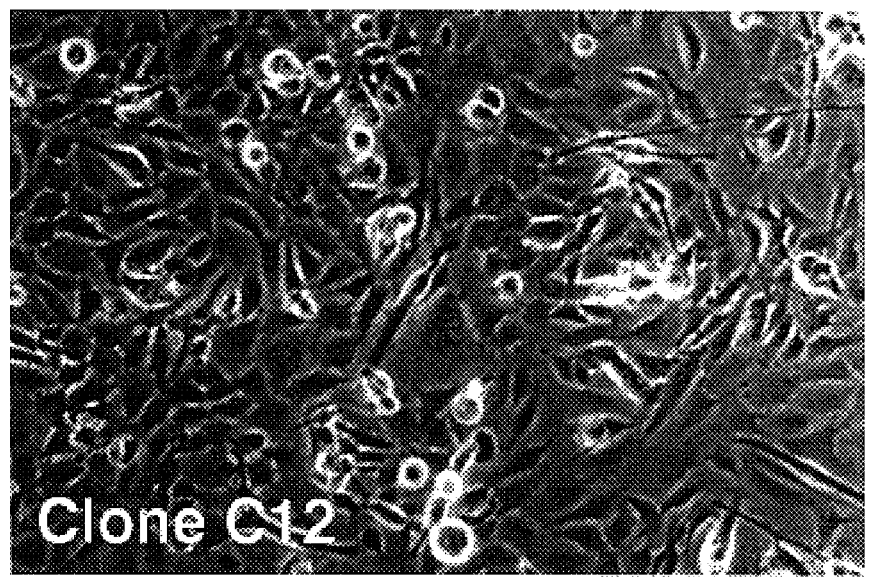
Figure 7A:
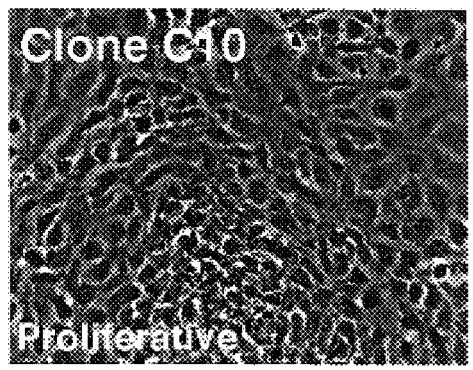
FIGS. 7A–7E illustrate the expression of v-myc in the representative clonal human DRG progenitor cell line C10.
Figure 7B:
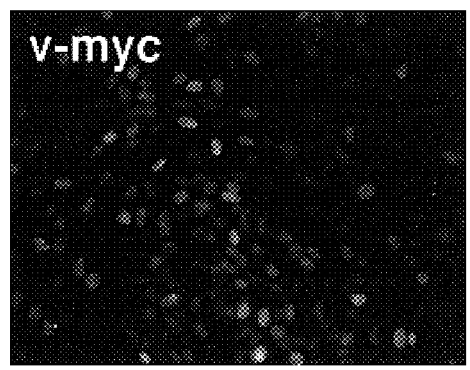
Figure 7C:
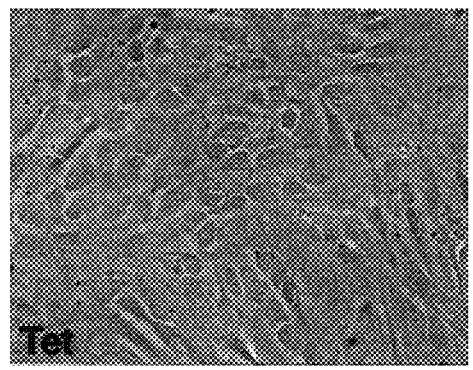
Figure 7D:
Figure 7E:
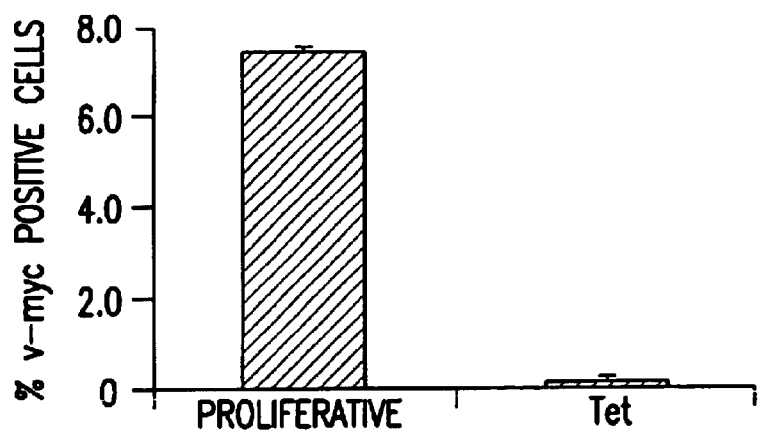

Morphology. The clones derived from HDRGVIII and HDRGIX all exhibited somewhat different morphologies. However, in general, the morphologies were similar to those of rat neural crest stem cells (FIG. 6).

Proliferation rate. All of the putative clones divided rapidly in the proliferative growth condition. Clone HDRGVIII-C10 could be expanded readily in the proliferative growth condition using L-1 SC growth medium plus FGF-2 (0.5–40 ng/mL), in which cells grow to high density and can be re-plated at low density. The substrate for proliferating HDRGVIII-C10 cells was fibronectin (16–100 μg/ml). In the proliferative growth condition, a typical confluent T75 flask contains approximately $10^7$ cells, which can be re-plated at a density of $5 \times 10^5$ cells per T75 (i.e., 1:20 split). An upper limit of 1.2 days for the doubling time of clone HDRGVIII-C10 has been calculated. Therefore, the clonal human immortalized PNS cell line HDRGVIII-C10 proliferates quickly under proliferative growth conditions.

Expression of regulatable v-myc. Immunocytochemistry for v-myc confirmed the presence of the oncogene in clone HDRGVIII-C10 and also established that the oncoprotein was effectively down-regulated by the addition of tetracycline to the growth medium (FIG. 7). In clone HDRGVIII-C10, 75±1.3% of the cells expressed the v-myc oncoprotein in the proliferative growth condition, whereas after 6 days of tetracycline treatment, the percentage of v-myc positive cells was suppressed to 1.1±0.8%. These data establish that the clonal human immortalized PNS cell line HDRGVIII-C10 expresses the oncogene v-myc under proliferative growth conditions, and that after treatment with tetracycline, oncogene expression can be repressed to 1.5% of proliferating levels.

Figure 9:
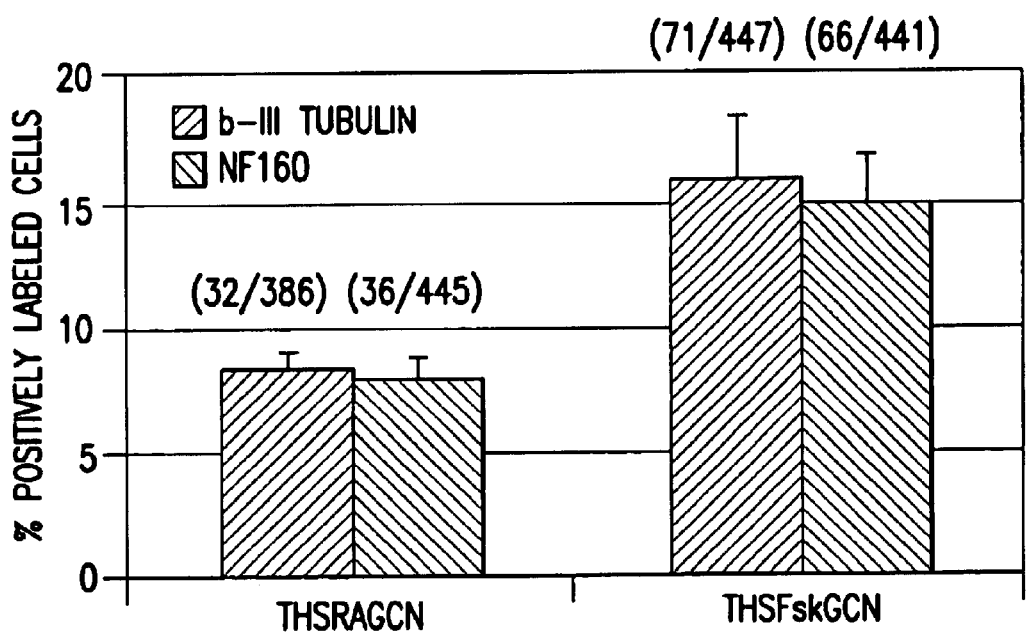
FIG. 9 is a histogram presenting the quantitation of neuronal markers in the clonal human DRG progenitor cell line C10 differentiated under different conditions. The percent of positively labeled cells for β-III tubulin (left column in each pair) and NF160 (right column in each pair) is shown. The left hand pair of columns shows the results for cells differentiated in the presence of tetracycline(1 μg/mL), human serum (2.5%), GDNF (25 ng/mL), CNTF (25 ng/mL), NGF (25 ng/mL) and retinoic acid (0.5 μM), and the right hand pair shows the results for cells differentiated in the presence of tetracycline, human serum, GDNF, CTNF, NGF and forskolin (10 μM).
Figure 8A:
FIGS. 8A–8C are photographs illustrating immunolabeling of the representative clonal human DRG progenitor cell line C10 following differentiation. Cells were labeled for β-III tubulin (FIG. 8A), NF160 (FIG. 8B) and substance P (FIG. 8C).
Figure 8B:
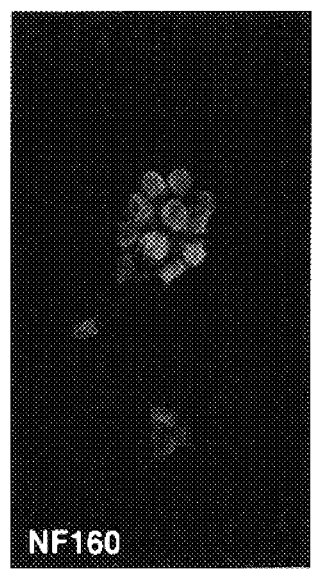
Figure 8C:
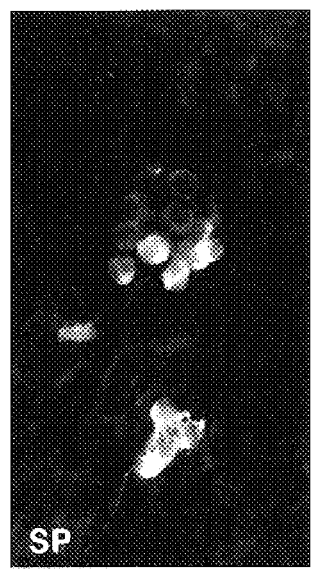

Neuronal differentiation. Clone HDRGVIII-C10 gave rise to neurons after differentiation for 10 days on a polyornithine/laminin substrate in medium containing tetracycline (1 μg/ml), human serum (2.5%), GDNF (25 ng/ml), CNTF (25 ng/ml) and NGF 25 ng/ml), plus either retinoic acid (0.5 μM) or forskolin (10 μM). After differentiation, phase-bright cells extending long fasciculating processes were present. Cells with neuronal morphology exhibited βIII tubulin- and NF160-immunoreactivities, confirming their neuronal phenotype, as well as substance P-immunoreactivity (FIG. 8). In both differentiation conditions, virtually all cells with neuronal morphology appeared to express NF160-immunoreactivity, suggesting that the neurons were mature after this 10 day differentiation period. Quantitation of immunostained cells in the 2 differentiation conditions is shown in FIG. 9. NF160 staining was observed in 15±2.2% of the cells grown in tetracycline (1 μg/ml), human serum (2.5%), GDNF (25 ng/ml), CNTF (25 ng/ml) and NGF (25 ng/ml), plus forskolin (10 μM) compared to 8.1%±0.8% of the cells grown in tetracycline (1 μg/ml), human serum (2.5%), GDNF (25 ng/ml), CNTF (25 ng/ml) and NGF (25 ng/ml), plus retinoic acid (0.5 μM).

These results indicate that parental (non-clonal) cultures of conditionally-immortalized human fetal DRG cells (HDRGVIII and HDRGIX) give rise to neurons after 1.5 weeks of differentiation, and that these neurons express βIII-tubulin (an early neuronal marker), NF160 (a mature neuronal marker), substance P (a neurotransmitter found in nociceptive neurons) and CGRP (a neurotransmitter found in nociceptive neurons). At least 10 distinct clonal cell lines have been isolated from human fetal DRG cells infected with the tetracycline-regulatable v-myc oncogene. In the proliferative growth condition, clonal immortalized human DRG cell lines exhibit morphology similar to rat neural crest stem cells and double in number within about one to one-and-a-half days.

HDRGVIII-C10 is a human clonal immortalized PNS cell line that exhibits the following properties:
- single, unique integration site of v-myc oncogene
- day doubling time in the proliferative growth condition
- v-myc in 75% of cells in the proliferative growth condition
- v-myc in 1% of cells after differentiation
- neuronal morphology after differentiation
- βIII-tubulin (early neuronal marker) after differentiation
- NF160 (mature neuronal marker) after differentiation
- substance P (nociceptive marker) after differentiation Example 3

Rat PNS Cell Line Development

This Example illustrates the conditional immortalization of rat neural crest stem cells and DRG neural precursor cells.

A. Immortalization of Neural Crest Stem Cells

Cultures of neural crest stem cells were successfully infected with the tetracycline-regulatable v-myc oncogene. It was necessary to modify the published protocol for culturing neural crest stem cells (Stemple and Anderson, Cell 71:973–985, 1992) in order to successfully infect neural crest stem cell cultures with the immortalizing oncogene. Specifically, in order to successfully infect neural crest stem cells, it was necessary to increase the concentration of FGF-2 from 4 ng/ml to 40 ng/ml, and eliminate retinoic acid, EGF and NGF from the published feeding medium. Embryonic day 10.5 rat neural tubes were dissected, dissociated partially with collagenase, and then plated into L-15C plus FGF-2 onto a fibronectin substrate. Cultures were infected for about 24 hours with amphotropic LINX v-myc retrovirus (from PA317 producer cells), and G418 selection was carried out in a manner similar to that used for establishing the human PNS lines. Putative clones were isolated with cloning rings after seeding cells at very low density in 100 mm dishes.

Figure 10A:
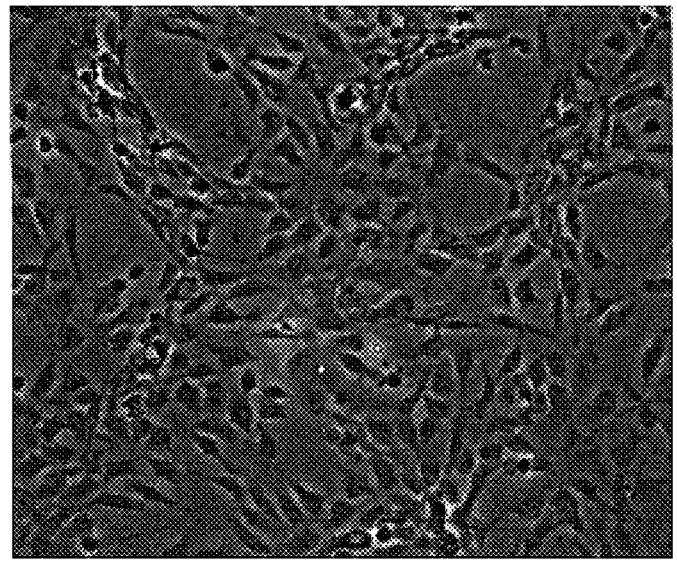
FIGS. 10A and 10B are photographs of representative conditionally-immortalized rat neural crest stem cells.
Figure 10B:
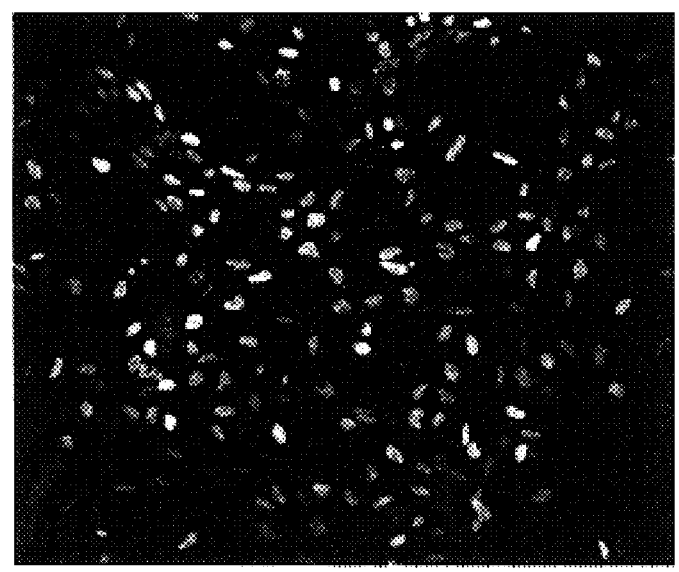
Figure 11A:
FIGS. 11A–11D are photographs illustrating the expression of β-III tubulin in representative conditionally-immortalized rat neural crest stem cells under different conditions. In each case, cells are immunolabeled for β-III tubulin.
Figure 11B:
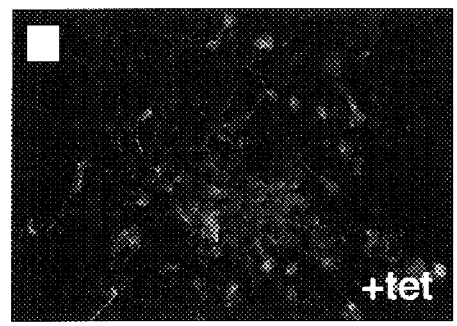
Figure 11C:
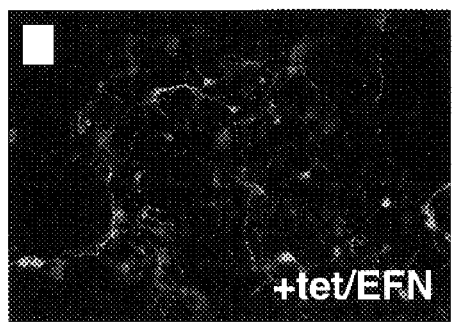
Figure 11D:
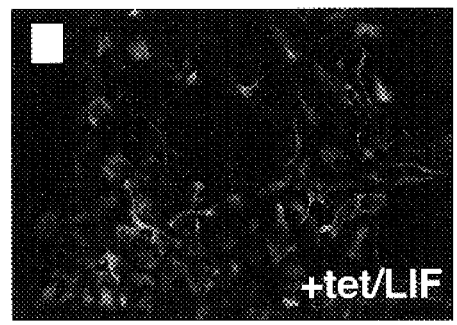

The cells exhibited nuclear v-myc immunoreactivity (FIG. 10), confirming that the retroviral infection had been successful. Some of the cells in the proliferative condition stained positively for βIII tubulin, a marker for immature neurons, suggesting that a neural progenitor was immortalized.

To differentiate the cells, we added tetracycline to the culture medium to suppress v-myc expression (FIG. 11). After 2 days of tetracycline treatment, the number of βIII tubulin immunoreactive cells increased from 1.9% in the proliferative condition to 11.9% when tetracycline was added. To promote further differentiation, cells were treated with tetracycline and the growth factors, EGF(100 ng/ml), FGF-2 (4 ng/ml) and NGF (2.0 ng/ml) (EFN), or LIF (100 ng/ml) for 5 days; the percentage of βIII tubulin positive cells increased further, to 18.6% and 28.4%, respectively. These data demonstrate that growth factors promote neuronal differentiation of immortalized neural crest stem cells.

These results indicate that several putative clones of immortalized rat neural crest stem cells have been isolated and expanded. Tetracycline and growth factor treatment increased substantially the number of βIII tubulin-immunoreactive cells. These data indicate that immortalized cells derived from the neural crest can be differentiated into neurons.

B. Immortalization of Rat DRG Neural Precursors

E12.5 rat DRGs were dissected, dissociated with collagenase and dispase, and then plated into L-15C plus FGF-2 (40 ng/ml) onto a fibronectin substrate. Cultures were infected for 13.5 hours with amphotropic LINX v-myc retrovirus (from PA317 producer cells) and G418 selection was carried out in a manner similar to that used for establishing the human PNS lines. Ten putative clones were isolated with cloning rings after seeding cells at very low density in 100 mm dishes.

In the proliferative state, immortalized rat DRG cultures express p75, βIII tubulin and vimentin immunoreactivities, but not NF160 immunoreactivity. To determine which trophic factors might be useful for differentiating the cells, RT-PCR was carried out to detect growth factor receptors present in the immortalized DRG cultures. PCR primers and conditions were validated on rat DRG tissue. Products of the correct size were found in immortalized rat DRG cultures for trkA, trkB and trkC, p75, c-RET, GDNFRα, gp130, CNTFRα, LIF-R and EGFR. Therefore, the ligands for these growth factor receptors were examined for the ability to promote neuronal differentiation.

Figure 12:
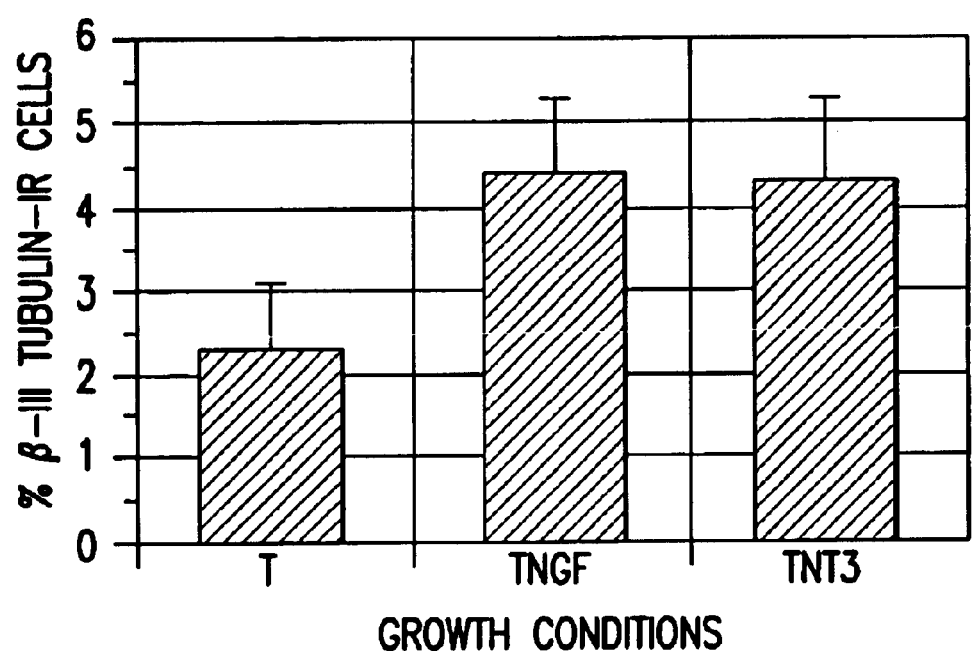
FIG. 12 is a histogram illustrating the expression of β-III tubulin in representative conditionally-immortalized rat DRG cultures under different conditions. Cells were immunolabeled for β-III tubulin, and the results are depicted as the percentage of β-III tubulin immunoreactive cells. Cells were grown in the presence of tetracycline (T; 1 μg/mL); tetracycline and NGF (TNGF; 20 ng/mL), or tetracycline (1 μg/mL) and NT-3 (TNT3; 20 ng/mL).
Figure 13:
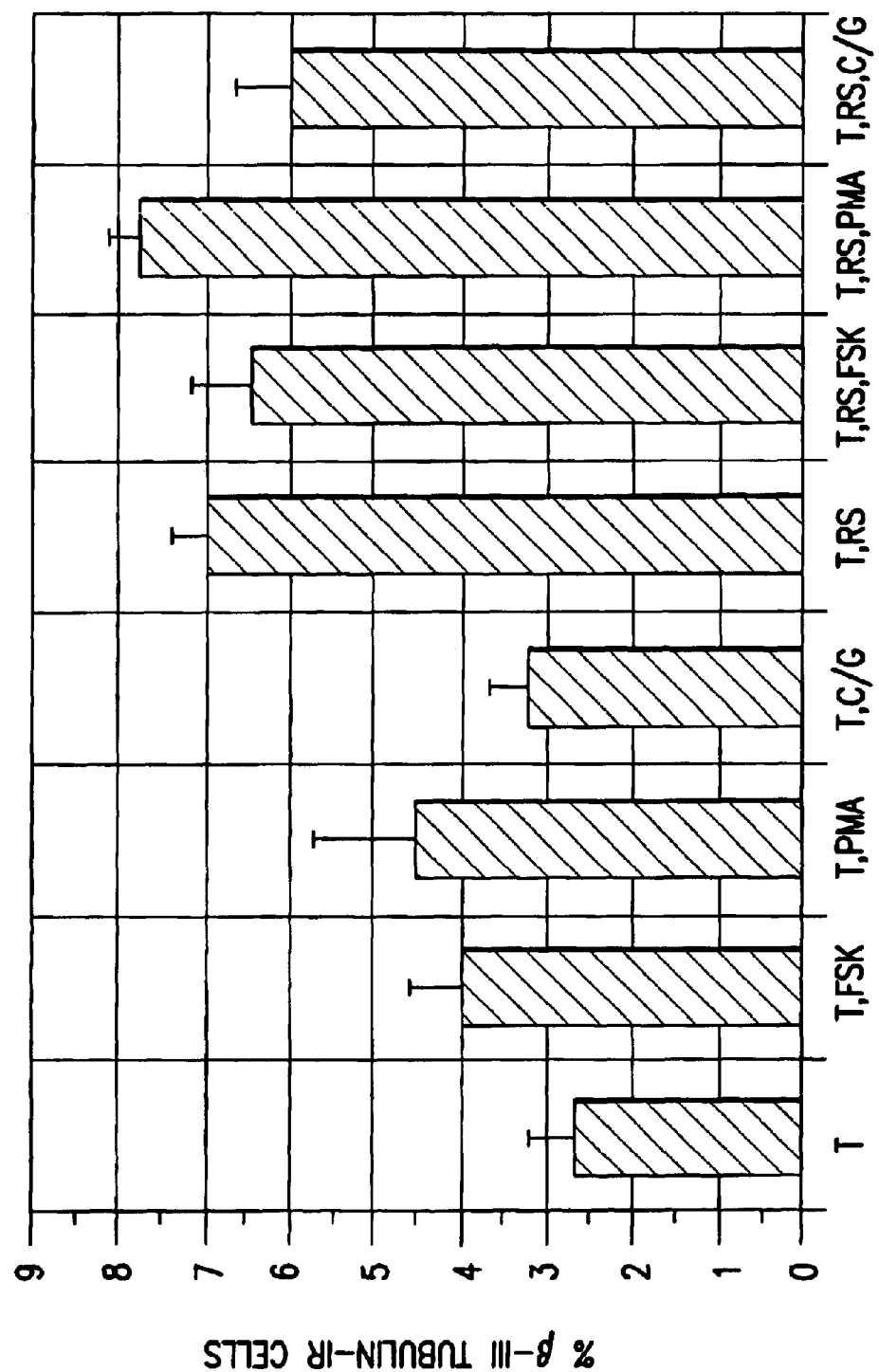
FIG. 13 is a histogram illustrating the expression of β-III tubulin in representative conditionally-immortalized rat DRG cultures under different conditions. Cells were immunolabeled for β-III tubulin, and the results are depicted as the percentage of β-III tubulin immunoreactive cells. Cells were grown in the presence of various combinations of tetracycline (T; 1 μg/mL), forskolin (FSK; 10 μM), PMA (20 nM), GDNF (C; 25 ng/mL), CNTF (C; 25 ng/mL) and/or rat serum (RS; 2.5%), as indicated.
Figure 14:
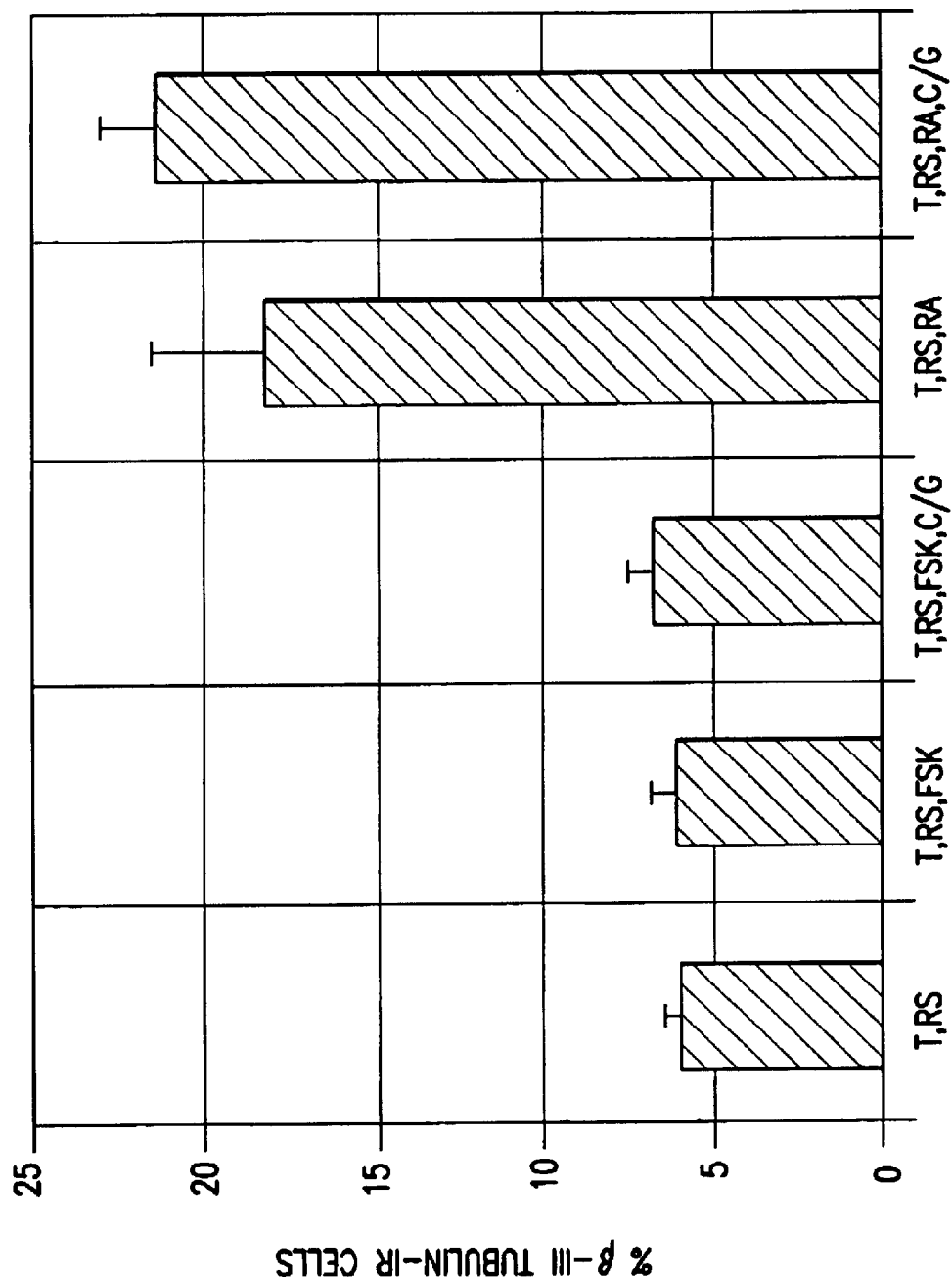
FIG. 14 is a histogram illustrating the expression of β-III tubulin in representative conditionally-immortalized rat DRG cultures under different conditions. Cells were immunolabeled for β-III tubulin, and the results are depicted as the percentage of β-III tubulin immunoreactive cells. Cells were grown in the presence of various combinations of tetracycline (T), forskolin (FSK; 10 μM), GDNF (G; 25 ng/mL), CNTF (C; 25 ng/mL), retinoic acid (RA; 0.5 μM) and/or rat serum (RS; 2.5%), as indicated.
Figure 15A:
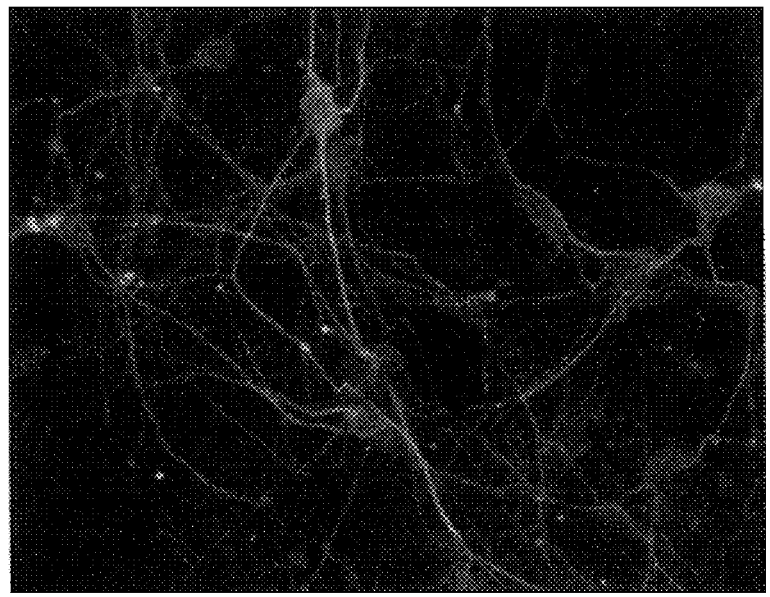
FIGS. 15A and 15B are photographs of conditionally-immortalized rat DRG cells differentiated for 1.5 weeks on a rat tail collagen substrate.
Figure 15B:
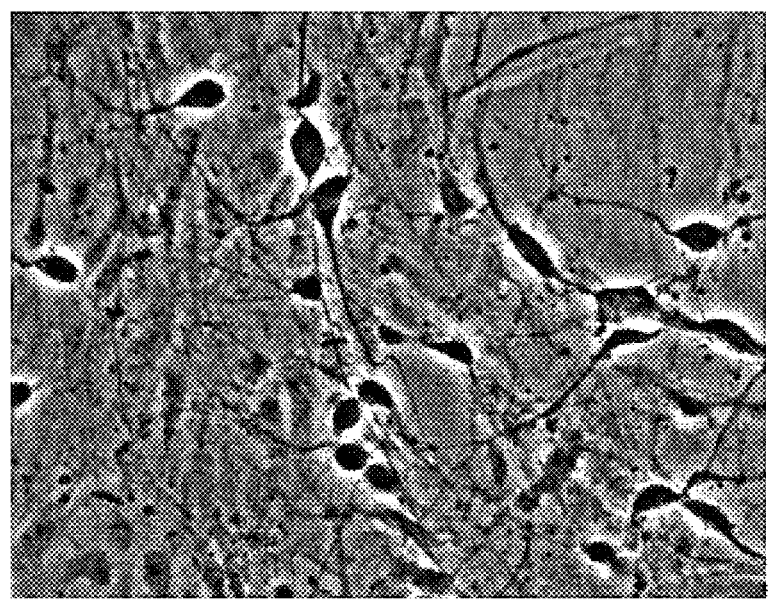
Figure 16:
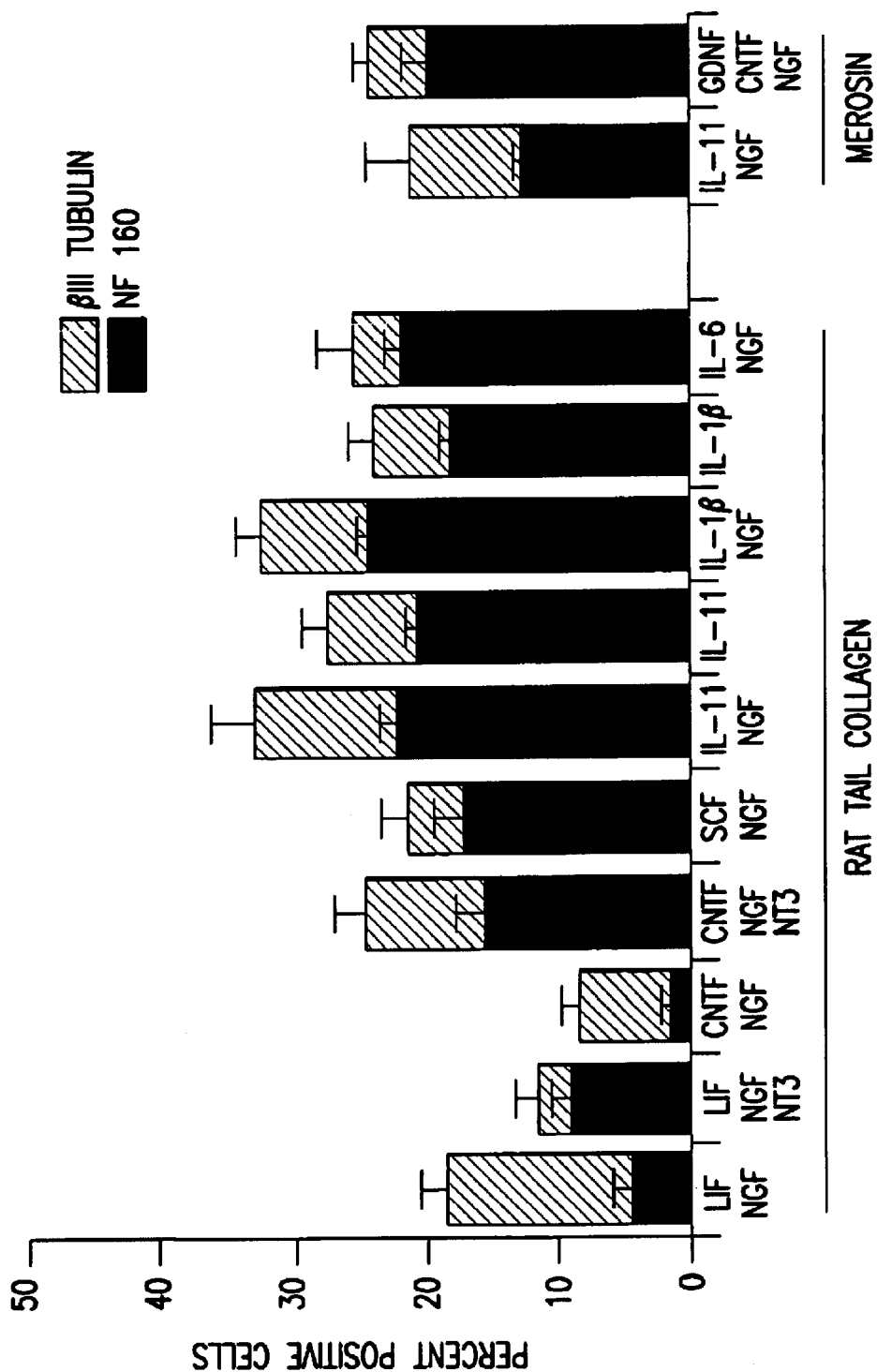
FIG. 16 is a histogram illustrating the expression of β-III tubulin and NF160 in representative conditionally-immortalized rat DRG cultures differentiated under different conditions. Cells were immunolabeled for β-III tubulin and NF160, and the results are depicted as the percentage of β-III tubulin- (cross-hatched bars) or NF160- (solid bars) immunoreactive cells. Cells were differentiated on rat tail collagen substrate or merosin, as indicated, and in the presence of tetracycline (1 μg/mL), rat serum (2.5%) and retinoic acid (0.5 μM), along with various combinations of leukemia inhibitory factor (LIF; 10 ng/mL)), nerve growth factor (NGF; 100 ng/mL)), NT-3 (10 ng/mL), CNTF (10 ng/mL), SCF (10 ng/mL), IL-11 (10 ng/mL), IL-1 β (10 ng/mL), IL-6 (10 ng/mL) and/or GDNF (10 ng/mL), as indicated.
Figure 17A:
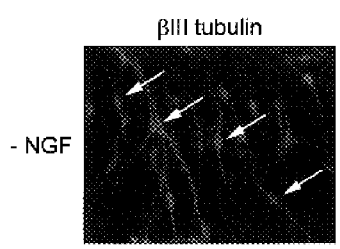
FIGS. 17A–17F are photographs illustrating the immunolabeling of β-III tubulin (FIGS. 17A and 17D), substance P (FIGS. 17B and 17E) and NF160 (FIGS. 17C and 17F) in representative conditionally-immortalized rat DRG cultures differentiated with tetracycline (1 μg/mL), rat serum (2.5%), retinoic acid (0.5 μM) and interleukin-1,β (IL-1β; 10 ng/mL), in the presence (FIGS. 17D–17F) or absence (FIGS. 17A–17C) of NGF (100 ng/mL). Arrows indicate cells that are double-labeled for β-III-tubulin and substance P.
Figure 17B:
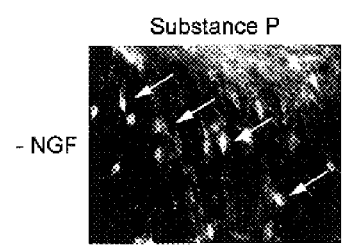
Figure 17C:
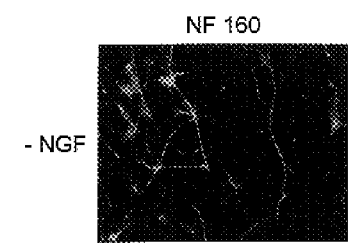
Figure 17D:
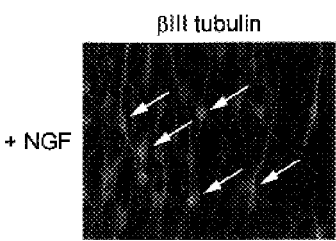
Figure 17E:
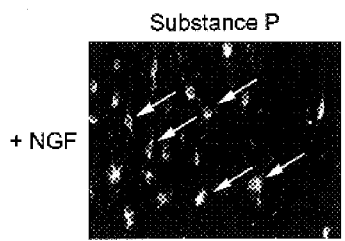
Figure 17F:
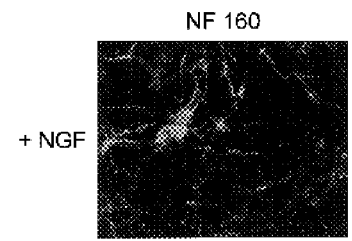

Many combinations of trophic factors as well as agents such as retinoic acid, forskolin, PMA and serum were examined for effects on neuronal differentiation of immortalized rat DRG cultures (FIGS. 12–14). The presence of rat serum (RS) and retinoic acid (RA) in the differentiation medium was found to be crucial for obtaining a high number of neurons. After differentiation with rat serun, retinoic acid and GDNF, CNTF, NGF, NT-3 plus BDNF, 24% of the immortalized rat DRG cells expressed the neuronal marker βIII tubulin. Furthermore, differentiation for 1.5 weeks on a rat tail collagen substrate enhanced neuronal maturation (expression of NF160) substantially (FIG. 15) compared with growth on polyomithinelamninin. Certain factors in combination with rat serum and retinoic acid on a rat tail collagen substrate increase the percentage of βIII tubulin cells to over 33% (FIG. 16). For example, after differentiation with interleukin-1,β (IL-1β) or IL-11 (10 ng/mL), in combination with NGF, 33% and 34% of the cells were βIII-tubulin positive, respectively (FIG. 16). In the absence of NGF, the percentage of βIII tubulin cells was slightly lower. Strong NF160 labeling was also observed in a fraction of these differentiated cells whereas substance P-immunoreactivity was present in all βIII-tubulin positive neurons (FIG. 17). These results indicate that IL-11 and IL-1β drive approximately a third of the cells into a neuronal lineage, and that this can be slightly augmented by the addition of NGF. NGF may act by promoting either neuronal differentiation or neuronal survival.

Differentiation with NGF plus leukemia inhibitory factor (LIF) or CNTF also resulted in a substantial, although somewhat lower percentage of βIII tubulin positive cells (FIG. 16). Interestingly, the addition of NT-3 to differentiation medium containing NGF plus either LIF or CNTF resulted in a striking increase in neuronal maturation (FIGS. 16 and 18). In the absence of NT-3, less than 25% of βIII tubulin positive cells expressed NF160. In contrast, in the presence of NT-3, 65% or more of the βIII tubulin positive cells expressed NF160. These results indicate that NT-3 promotes the maturation of neuronal precursors.

These results indicate that that trkA, trkB, trkC, p75, c-RET, GDNFRα, CNTFRα, LIF-R and gp130 are present in the immortalized DRG precursors. Differentiation conditions consisting of the neurotrophins and cytokines, and additional agents such as serum, retinoic acid, forskolin and PMA, have been tested, and conditions were identified that dramatically increase the number of βIII tubulin positive neurons to ~34% vs. ~2.5% in tetracycline alone. Conditions particularly beneficial for differentiation include tetracycline, rat serum (2.5%), retinoic acid (0.5 μM) and NGF, plus either IL-11 or IL-1β, in combination with a rat tail collagen substrate. One-third of the cells are βIII tubulin positive in these conditions. The addition of NT-3 dramatically increased the percentage of cells expressing NF160, a marker for mature neurons, indicating that NT3 promotes neuronal maturation.

Example 4

Electrophysiological Characterization of Conditionally Immortalized DRG Cells This Example illustrates the electrophysiological properties of conditionally-immortalized rat and human DRG cells after differentiation.

Conditionally-immortalized human and rat DRG cells were grown on polyornithine/laminin and rat tail collagen-coated dishes, respectively, and differentiated for 1 to 4 weeks. Cells with neuronal morphology were selected for whole-cell patch clamp recording.

In order to record action potentials or to isolate specific types of voltage- and ligand-gated currents, 3 different internal solutions (Table 2) were used in conjunction with 2 types of external solution. The bath solution was 2 Ca Tyrode's solution containing (in mM) 2 $CaCl_2$, 150 NaCl, 4 KCl, 2 $MgCl_2$, 10 Glucose, 10 HEPES, pH 7.4 with NaOH plus 1–3 units/ml of apyrase.

TABLE 2

Solutions Used for Isolation of Different Electrophysiological Responses

| Response | Internal Solution | Specific Internal Solution Components (in mM)[a] | | External Solution (in mM) |
|---|---|---|---|---|
| $I_{Na}$ | TEA-F | 120 TEA-F | | 2 Ca Tyrode's |
| $I_K$, AP[b] | KCl | 120 KCl | | 2 Ca Tyrode's |
| $I_{ATP}$, $I_{caps}$ | $CsCH_3SO_3$ | 120 nucleotide solution | $CsCH_3SO_3$, regenerating | 2Ca Tyrode's |
| $I_{Ca}$, $I_{Ba}$ | $CsCH_3SO_3$ | 120 nucleotide solution | $CsCH_3SO_3$, regenerating | 160 TEA-Cl, 5 or 10 $CaCl_2$ or $BaCl_2$, 10 HEPES, pH 7.4, 0.5–1 µM TTX |

[a]common internal solution components (in mM): 5 $MgCl_2$, 10 HEPES, 10 EGTA, pH 7.4
[b]action potential In proliferating immortalized rat DRG cultures, no voltage-gated sodium current or ATP-activated current was observed, as expected (n=15).

Figure 19:
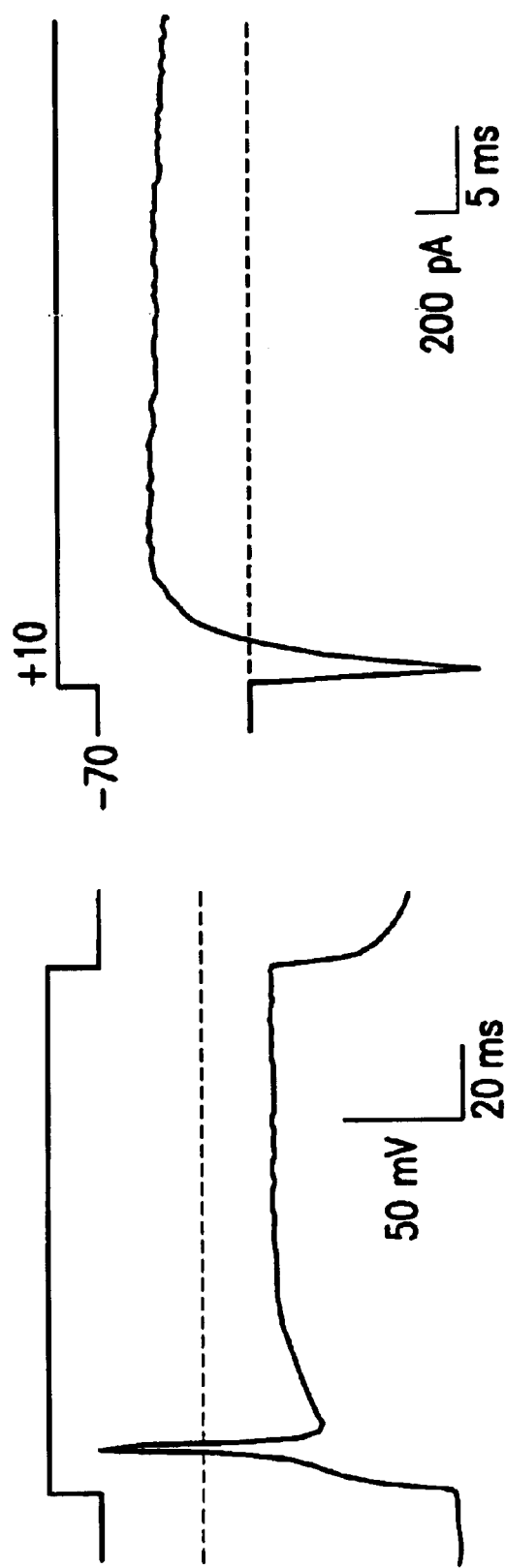
FIG. 19 depicts the results of electrophysiological recordings from representative differentiated conditionally-immortalized human DRG cells. In the left-hand panel, an action potential in response to current injection is shown. In the right-hand panel, a depolarizing step in the membrane potential from −70 to +10 mV elicits a rapid inward current followed by a sustained outward current, probably carried by sodium and potassium ions, respectively.
Figure 20:
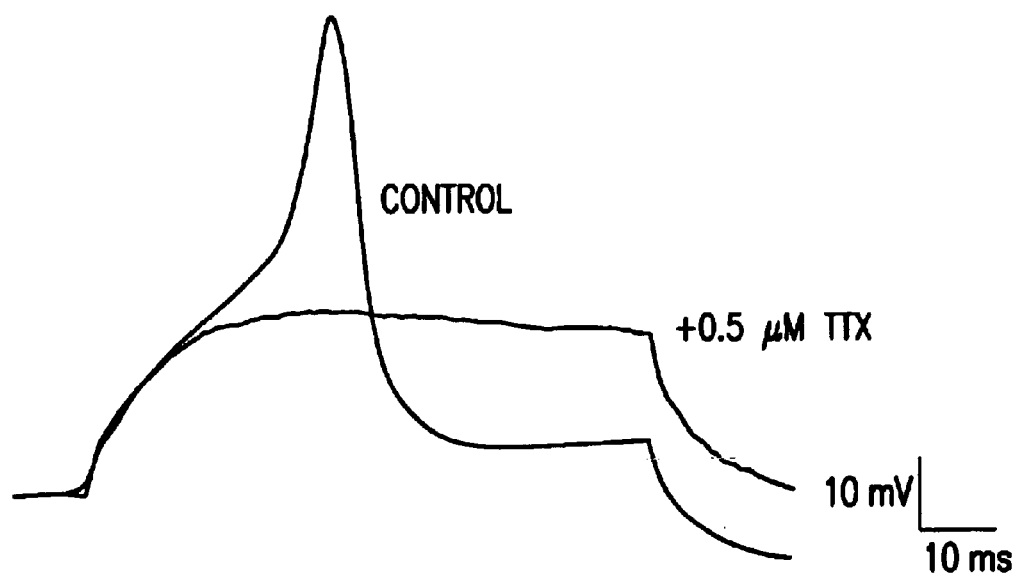
FIG. 20 depicts an action potential recorded from a representative differentiated conditionally-immortalized rat DRG cell (control). In response to current injection, an action potential is fired (control), which is blocked by 0.5 μM tetrodotoxin (TTX).

Action potentials. After differentiation, conditionally-immortalized human (FIG. 19) and rat (FIG. 20) DRG cells (17/17 cells) with neuronal morphology fired action potentials in response to current injection. With KCl as the internal solution, depolarizing voltage steps from –70 to +10 mV elicited rapid inward currents followed by sustained outward currents, presumably carried by sodium and potassium, respectively. TTX, at 0.5 to 1 µM, blocked the action potentials as well as the inward currents in these cells. Nevertheless, the ability to fire action potentials further confirms the neuronal phenotype of the differentiated cells, consistent with their neuronal morphology and immunocytochemical staining for neuron-specific markers (see above).

Sodium current. After differentiation of immortalized rat DRG cells for ~1 week with tetracycline, rat serun (2.5%), retinoic acid (0.5 µM) and trophic factors (GDNF, CNTF, NGF, NT-3 and/or BDNF), most cells (62%) with neuronal morphology exhibited voltage-gated sodium currents that were TTX-sensitive.

Figure 21:
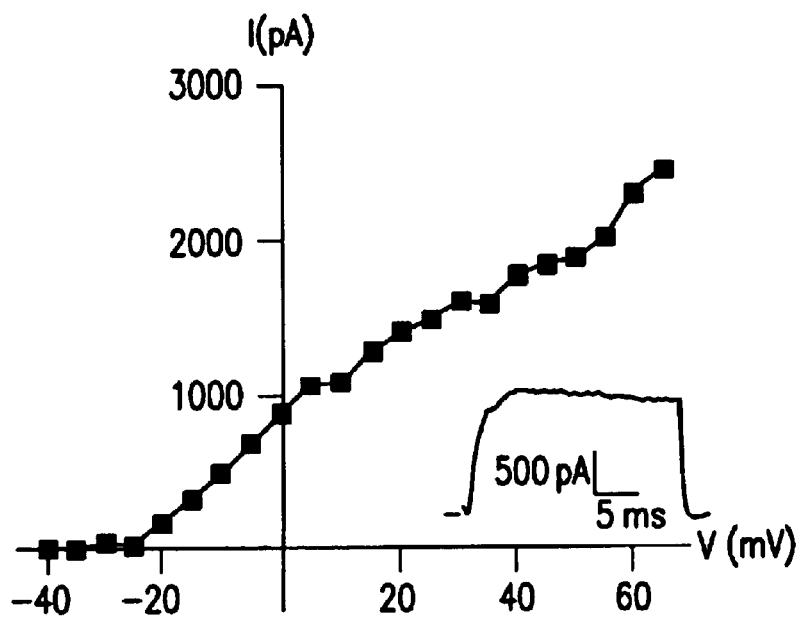
FIG. 21 depicts the results of recording potassium currents from a representative differentiated conditionally-immortalized rat DRG cell. The cell was depolarized to membrane potentials from −40 to +65 mV; current amplitudes (I) are shown as a function of the test potential (V).

Potassium current. The potassium current in differentiated immortalized rat DRG cells is sustained and begins to activate at –25 mV (FIG. 21). These properties are consistent with the delayed rectifier potassium current.

Figure 22:
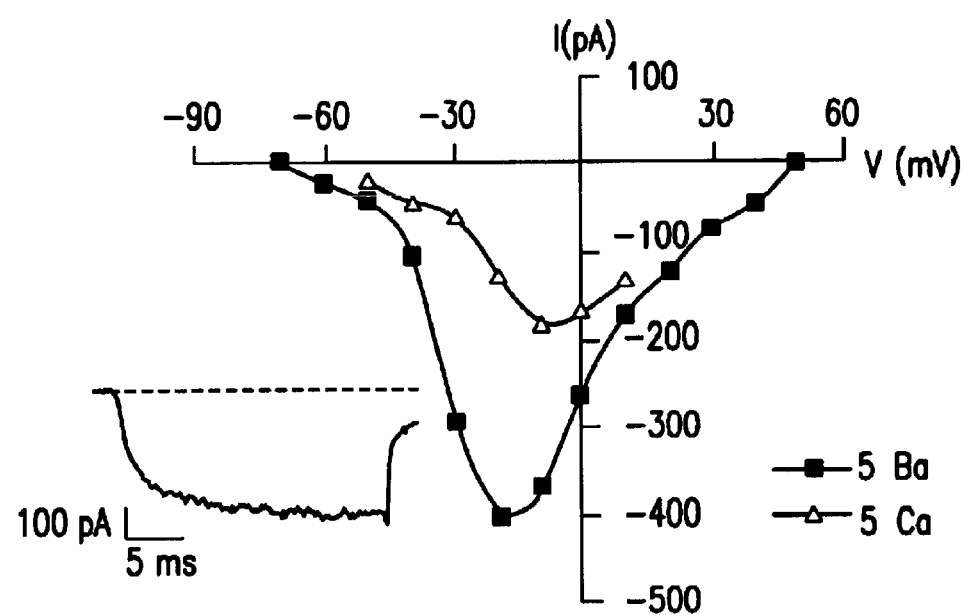
FIG. 22 depicts the results of recording calcium currents from a representative differentiated conditionally-immortalized rat DRG cell. The cell was depolarized to membrane potentials from −70 to +50 mV; current amplitudes (I) are shows as a function of the test potential (V) with 5 mM calcium (5 Ca) or 5 mM barium (5 Ba) as the charge carrier.
Figure 23:
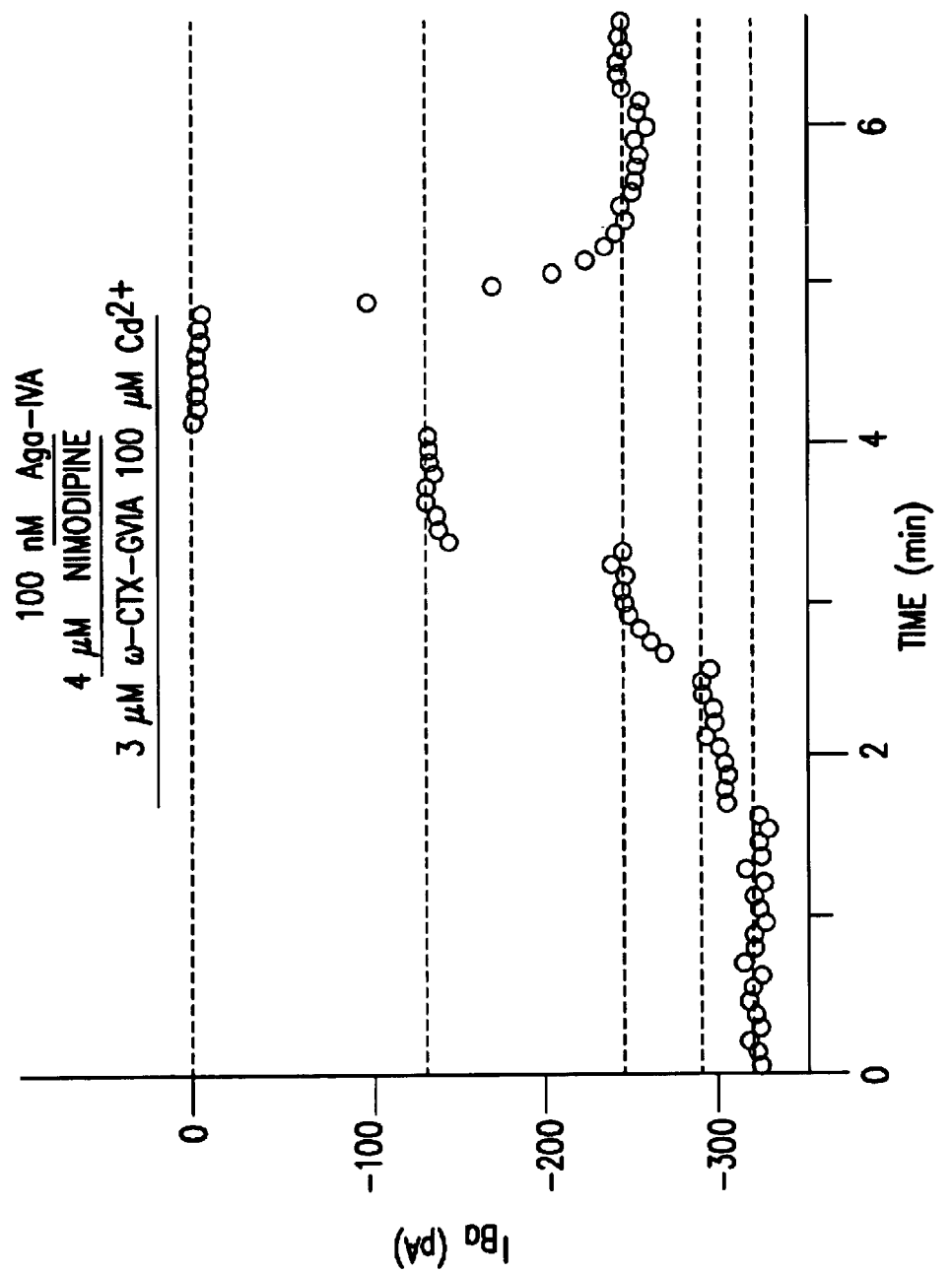
FIG. 23 depicts the results of electrophysiological analysis of voltage-gated calcium current in a representative differentiated conditionally-immortalized rat DRG cell. The effect on calcium channel current amplitude of treatment with various compounds is shown as indicated.

Calcium current. Calcium channel current (882±315 pA; depolarization from –80 to –10 mV) was observed in 5 of 8 differentiated immortalized rat DRG cells with 5–10 mM $Ba^{2+}$ as the charge carrier. The current carried by $Ba^{2+}$ through the channel was substantially larger than that carried by $Ca^{2+}$ (FIG. 22). The pharmacology of this current indicates that it is mediated by N-, L- and P-type calcium channels, sensitive to block by 3 µM ω-CTX-GVIA, 4 µM nimodipine and 100 nM ω-Aga-IVA, respectively (FIG. 23).

Figure 24:
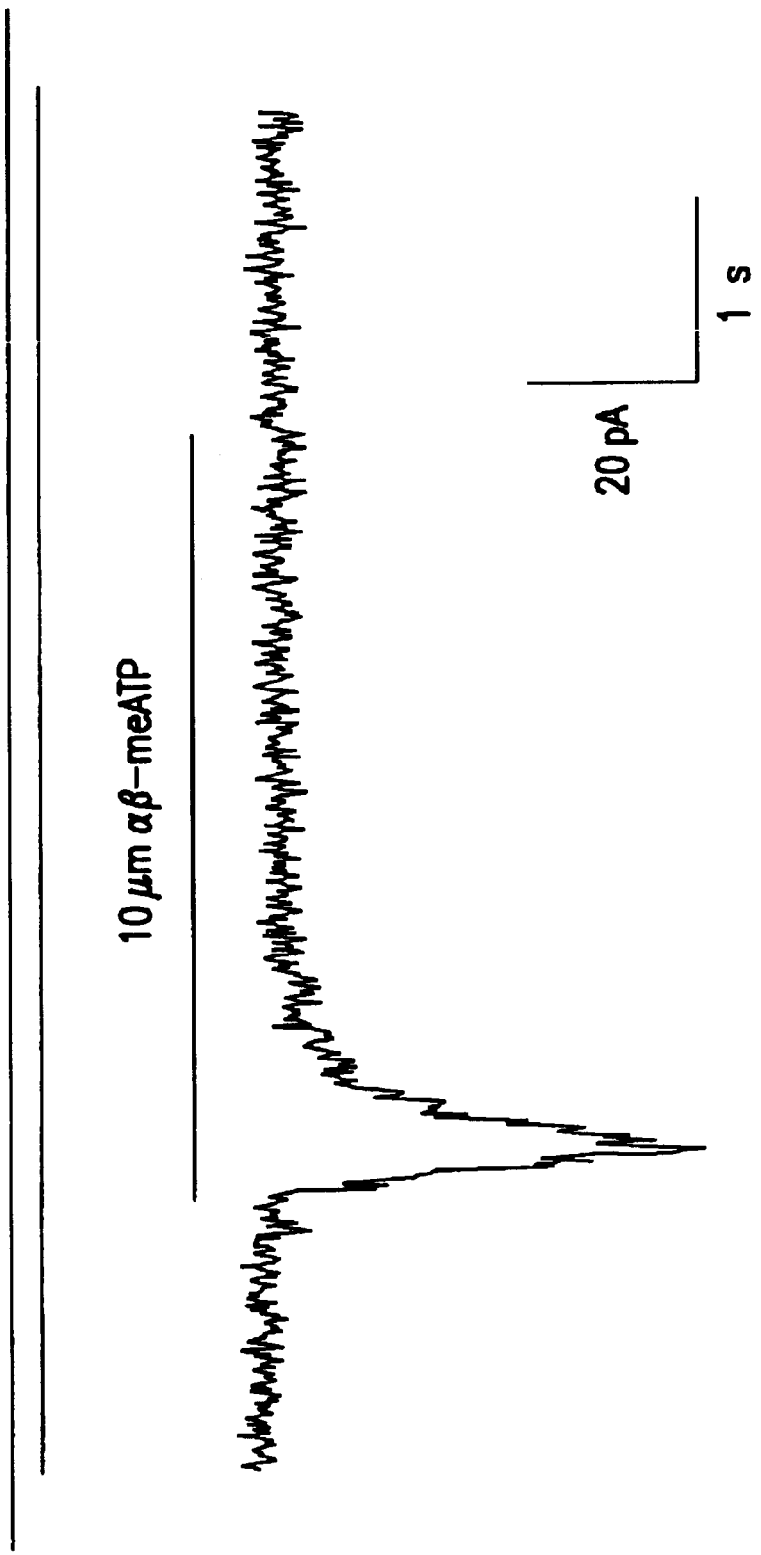
FIG. 24 depicts the electrophysiological response to αβ-methylene-ATP of a representative differentiated conditionally-immortalized human DRG cell.

ATP current. In immortalized human PNS cell line HDRGVIII-C10, differentiated for 1–2 weeks with tetracycline (1 µg/ml) human serum (2.5%), GDNF (25 ng/ml), CNTF (25 ng/ml) and NGF (25 ng/ml), plus forskolin (10 µM), all cells with neuronal morphology exhibited ATP responses. Rapidly activating and strongly desensitizing currents were elicited by 10 µM αβ-meATP (FIG. 24).

Figure 25:
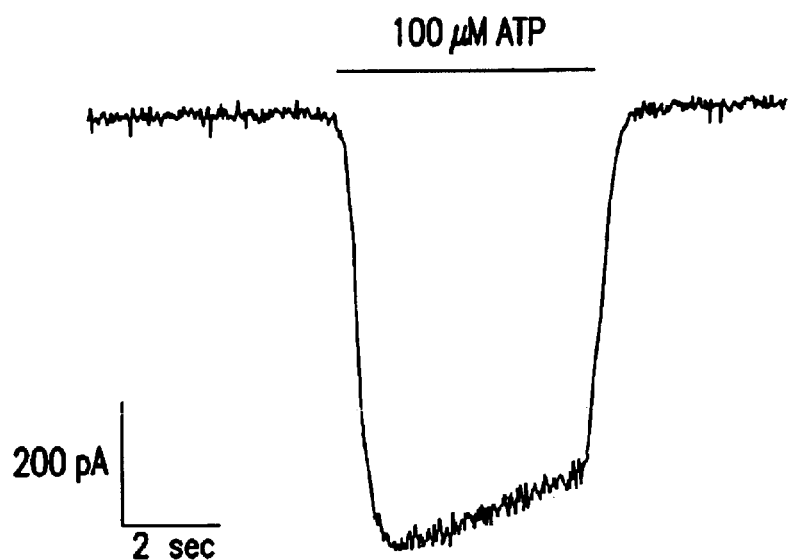
FIG. 25 depicts the electrophysiological response to ATP of a representative differentiated conditionally-immortalized rat DRG cell.

In immortalized rat DRG cells differentiated for 3–4 weeks with tetracycline, rat serum, retinoic acid, NGF, and in some cases, GDNF plus CNTF, non-desensitizing ATP responses were present in cells with neuronal morphology. 5-second applications of 100 µM ATP (FIG. 25) or αβ-meATP elicited currents with only ~15% desensitization. The expression of ATP-activated current depended on the length of differentiation. After 1 week of differentiation, no cells (n=14) showed ATP-activated current, whereas after 3 weeks of differentiation, ~30% of cells (5/17 cells) had ATP-activated current. αβ-meATP responses remained rare, however, and have been observed in only 1 of 20 cells so far.

Figure 26:
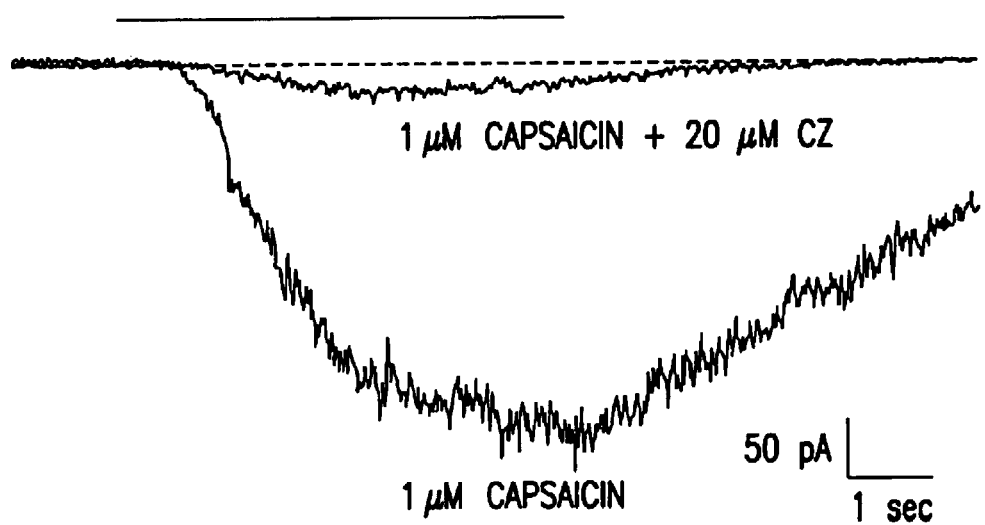
FIG. 26 depicts the electrophysiological response to capsaicin of a representative differentiated conditionally-immortalized human DRG C10 cell. The antagonist, capsazepine (CZ), inhibited the response.

Capsaicin current. Differentiated cells with neuronal morphology from immortalized human PNS cell line HDRGVIII-C10 exhibited responses to 1 µM capsaicin which were blocked by 20 µM capsazepine (FIG. 26). Prior to differentiation, no immortalized human PNS HDRGVIII-C10 cells exhibited responses to capsaicin. In contrast, differentiated immortalized rat DRG cells did not exhibit responses to capsaicin (n=6).

Figure 27:
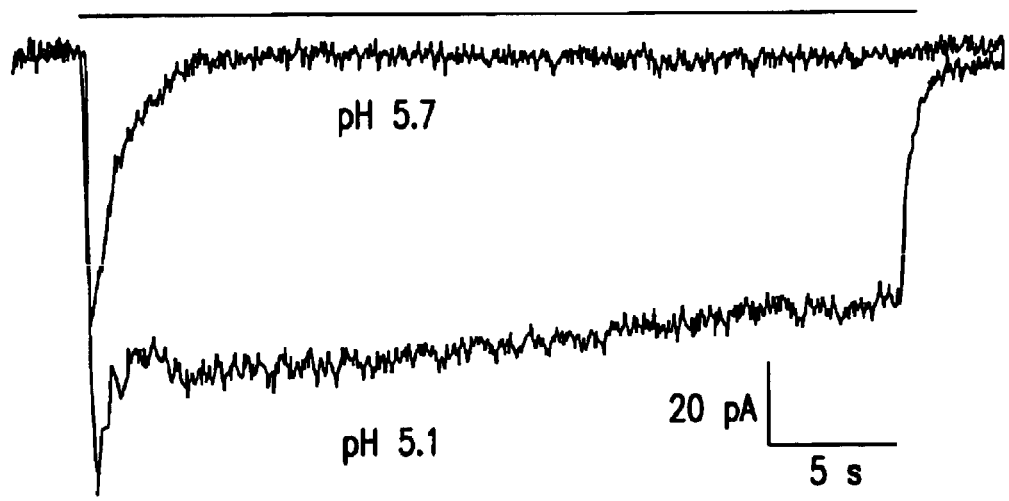
FIG. 27 depicts $H^+$-gated currents in a representative differentiated conditionally-immortalized human DRG C10 cell.
Figure 28:
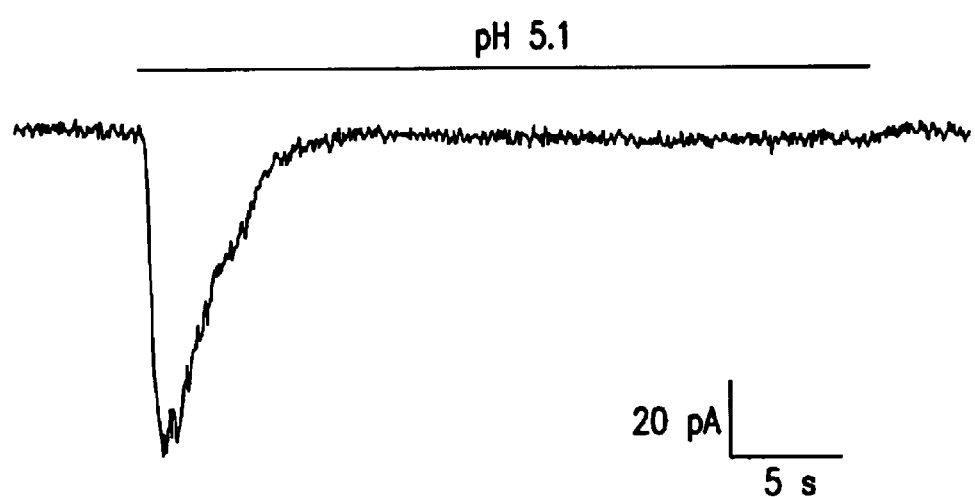
FIG. 28 depicts $H^+$-gated currents in a representative differentiated conditionally-immortalized rat DRG cell.

Proton-gated current. Differentiated cells with neuronal morphology from immortalized human PNS cell line HDRGVIII-C10 exhibited inward currents in response to a step to low pH (e.g., pH 4.5–5.7) from pH 7.4, that contained transient and sustained components (FIG. 27). Transient and sustained proton-gated currents were also present prior to differentiation of immortalized human PNS HDRGVIII-C10 cells. Differentiated immortalized rat DRG cells also exhibited proton-gated currents (FIG. 28).

These results indicate that, after differentiation, immortalized human DRG cells with neuronal morphology expressed action potentials. In addition, HDRGVIII-C10 is a human clonal immortalized PNS cell line that exhibits the following properties:

voltage-gated sodium current after differentiation
αβ-meATP current after differentiation
capsaicin-activated current after differentiation
proton-activated current after differentiation After differentiation, immortalized rat DRG cells with neuronal morphology expressed the following properties.

action potentials
sodium currents
potassium currents
calcium currents (L-, N- and P-types)
ATP currents
proton-activated currents The presence of these functional properties further confirms the neuronal phenotype of the differentiated immortalized DRG cells. Furthermore, the presence of functional capsaicin receptors confirms the nociceptive neuronal phenotype of HDRGVIII-C10.

Example 5

Further Development of Human PNS Cell Sines

This Example illustrates the development of additional human clonal conditionally-immortalized PNS cell lines that differentiate into neurons.

A. Subclones of HDRGVIII-C10

Figure 29:
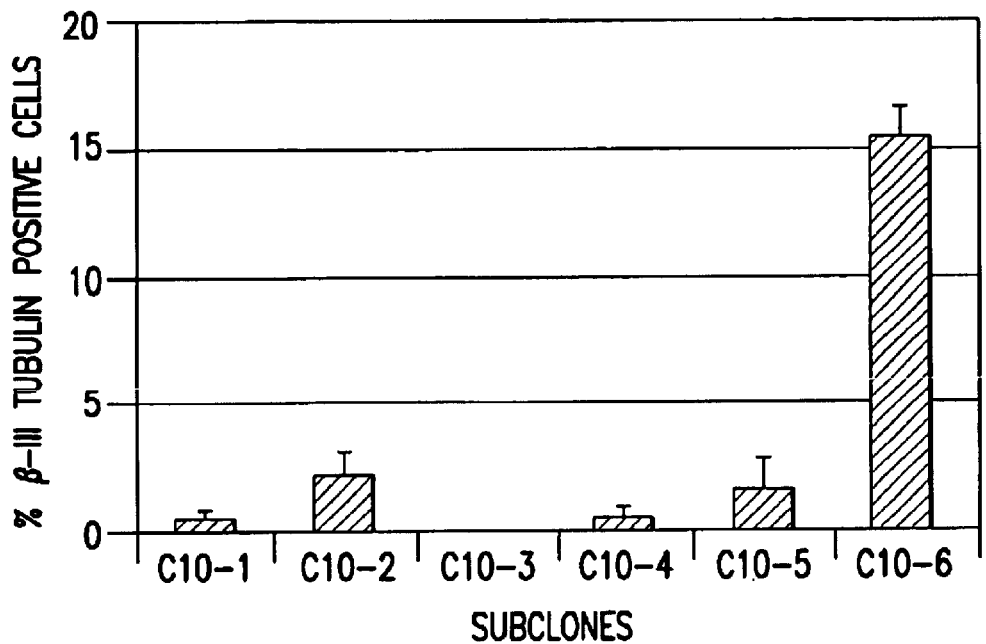
FIG. 29 is a histogram illustrating the immunolabeling of β-III tubulin in proliferative human DRG C10 cell line subclones. The mean percentage of cells that exhibited 0111-tubulin expression is presented for subclones HDRGVIII-C10.1, -C10.2, -C10.3, -C10.4, -C10.5 and -C10.6, as indicated.
Figure 30:
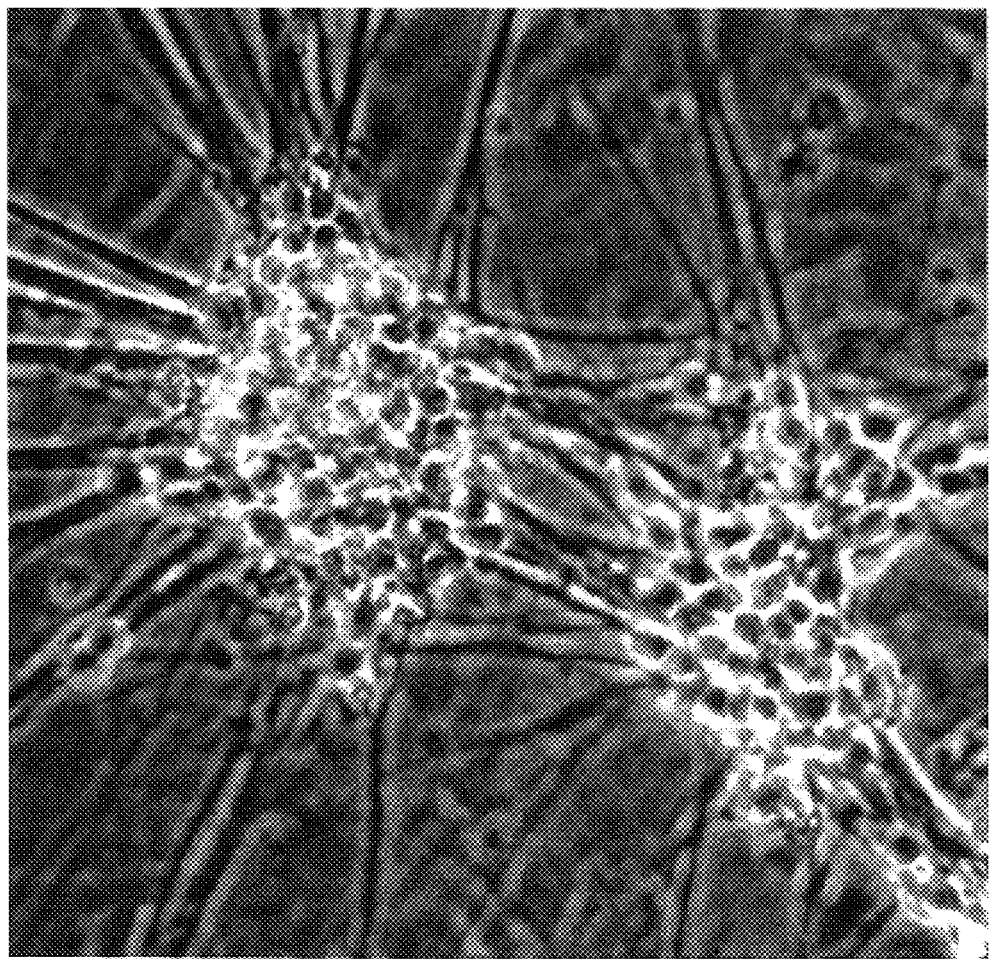
FIG. 30 is a photograph of HDRGVIII-C10.6 cells following differentiation with tetracycline, human serum, forskolin, GDNF, CTNF and NGF.

Optimization of neuronal differentiation. To increase the number of neurons following differentiation, we isolated 6 strains or sub-clones of HDRGVIII-C10. The 6 sub-clones exhibit doubling times that are approximately the same as the parental line, HDRGVIII-C10. In addition, the 6 sub-clones were examined for v-myc regulation by tetracycline; in all cases, the oncoprotein was suppressed by differentiation with tetracycline as expected. Since the presence of the marker βIII-tubulin in the proliferative condition is generally predictive of neuronal differentiation, the 6 subclones for βIII-tubulin were immunolabeled in the proliferative growth condition; the mean percentage of cells that exhibited βIII-tubulin expression ranged from 0% in sub-clone HDRGVIII-C10.3 (as with HDRGVIII-C10) to 15.5% for HDRGVIII-C10.6 (FIG. 29). Consistent with the high expression of βIII-tubulin in HDRGVIII-C10.6 in the proliferative growth condition, HDRGVIII-C10.6 appeared to have the most neurons (>50%) based on morphology, after differentiation with T, HS, Fsk, G, C, plus N (FIG. 30).

Figure 31:
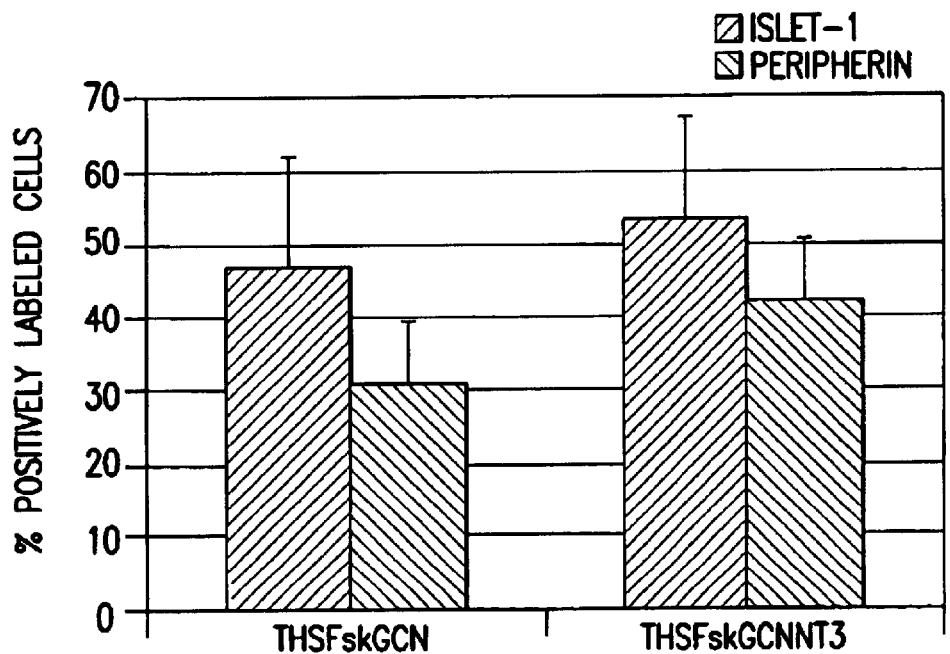
FIG. 31 is a histogram illustrating the expression of Islet-1 and peripherin in proliferative and differentiated human DRG C10.6 cell line subclones. The mean percentage of cells that immunolabeled for Islet-1 (left columns in each pair) and peripherin (right columns in each pair) are shown for cells differentiated with tetracycline (1 μg/mL), human serum (2.5%), forskolin (10 EM), GDNF (25 ng/mL), CTNF (25 ng/mL) and NGF (25 ng/mL), in the presence (right hand pair) and absence (left hand pair) of NT-3 (25 ng/nL).
Figure 32:
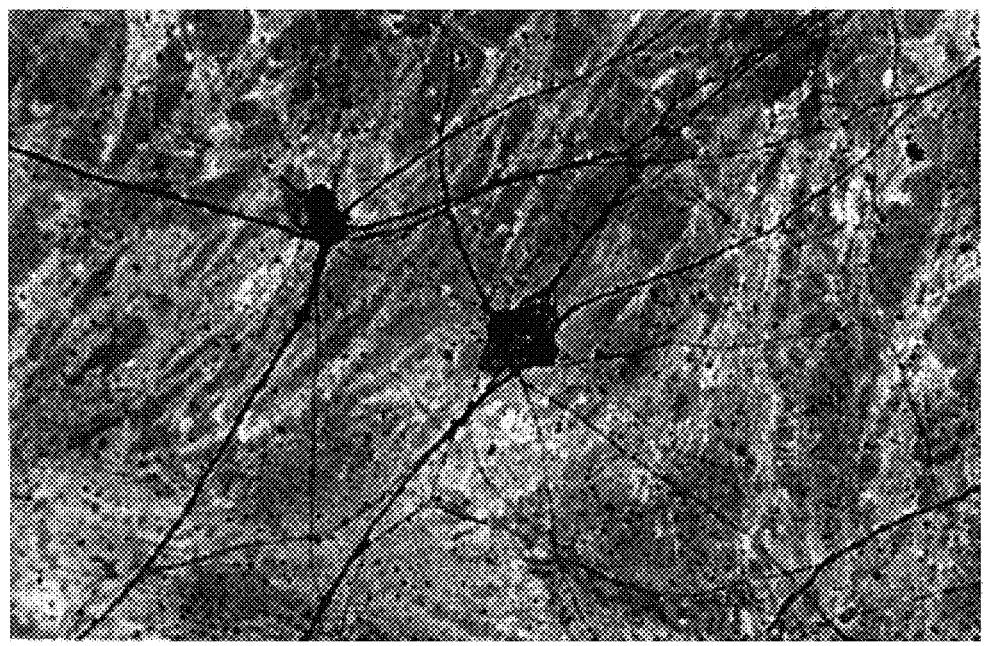
FIG. 32 is a photograph of a capsaicin stimulated culture of the human DRG C10.6 subclone, showing cobalt uptake.

Characterization of sensory neuronal differentiation. To assess sensory neuronal differentiation, we examined the effects of different substrates and culture conditions on the expression of Islet-1, peripherin and capsaicin sensitivity. Islet-1 is a homeobox, lim-domain transcription factor that is expressed in DRG cells early during differentiation. In the PNS of the Islet-1 knockout mouse, DRGs fail to form (Pfaff et al., *Cell* 84;309–320, 1996), indicating that Islet-1 has a critical functional role in the development of sensory neurons. Since Islet-1 is required for sensory neuron development in vivo, we examined the presence of Islet-1 in the human PNS lines. HDRGVIII-C10.6 cells were cultured for 5 days in the presence of T, HS, Fsk, G, C, plus N with or without NT-3 (25 ng/ml), and examined for the expression of Islet-1 and peripherin and capsaicin sensitivity. Islet-1 was expressed in the nuclei of approximately 50% of all HDRGVIII-C10.6 cells after differentiation with T, HS, Fsk, G, C, plus N, whether or not NT-3 was present (FIG. 31). After differentiation, of the cells with neuronal morphology, most expressed Islet-1 immunoreactivity. The mature neuronal marker, peripherin, was expressed by 31±9% and 43±8% of the cells after differentiation with T, HS, Fsk, G, C, plus N, and T, HS, Fsk, G, C, N, plus NT-3, respectively (FIG. 31). After differentiation, of the cells with neuronal morphology, most expressed peripherin immunoreactivity and NT-3 appears to marginally increase the percentage of neurons differentiating from HDRGVTIII-C10.6. Cobalt histology (see Wood et al., *J. Neurosci.* 8:3208–3220, 1988) was used to detect capsaicin sensitivity in HDRGVIII-C10.6 cells differentiated for 7 days on a polyornithine/laminin substrate in the presence of T, HS, Fsk, G, C, N, plus NT-3 (FIG. 32). Following exposure to 10 μM capsaicin, 30.8±2.9% of the cells with neuronal morphology exhibited cobalt uptake.

Stability. The clonal human PNS cell line HDRGVIII-C10.6 expresses equivalent levels of the three cell type specific markers βIII-tubulin, NF160 and GFAP at an early passage (passage 5) compared to a much later passage (passage 20), after differentiation. It is estimated that approximately 65 doublings or generations occurred between passages 5 and 20. After differentiation for 4.5–5 days with tetracycline (1 μg/mL), human serum (2.5%), forskolin (10 μM), GDNF (25 ng/mL), CNTF (25 ng/mL) and NGF (50 ng/mL), the percentages of immunostained cells at passages 5 are 56±2% βIII-tubulin-positive, 42±7% NF160-positive and 0% GFGAP positive. Similarly, at passage 20, the percentages of immunostained cells are 61±8% βIII-tubulin-positive, 42±6% NF160-positive and 0% GFAP-positive.

In addition, by genomic Southern analysis of HDRGVIII-C10.6, the DNA fragment size that hybridizes to a v-myc probe, after HindIII restriction digest, is 4.7 kb, as expected. Moreover, single bands of the same size resulted from passage 3 and passage 17 cultures of HDRGVIII-C10.6. These results establish that the site of v-myc integration in clone HDRGVIII-C10.6 is stable across approximately 65 cell generations.

B. Characterization of Additional HDRGVIII Clones

Clones C1, C2, C5, C7, C11, C18, C22, C23 and C26 were characterized further. In the proliferative condition, clones C1, C2, C5, C11, C18, C22, C23 and C26 were positive for p75 and v-myc, and negative for GFAP. In contrast, proliferative clone C7 did not contain any cells positive for p75. In the proliferative condition, βIII tubulin-immunoreactive cells were detected in clones C1 (faint staining), C2 and C11. After differentiation, clones C2, C11 and C22 gave rise to neurons, based on morphology and immunoreactivity for βIII-tubulin, NF160 and peripherin. The neurons generally aggregated into clusters of 3 or more cells, with their processes forming long fascicles. All of the cells with neuronal morphology expressed βIII-tubulin and NF160, and approximately 82–85% of the neurons also expressed substance P.

C. HDRGVIII-C11

Optimization of neuronal differentiation: effects of NT-3 and IL-11. To determine if NT-3 increased the number of neurons that differentiated from immortalized human DRG cells, clone-C11 was differentiated in the presence or absence of NT-3, and then scored for the percentage of βIII-tubulin-positive neurons. When NT-3 was added to the standard differentiating medium, 4.0±2.2% of C11 cells differentiated into neurons, a slight increase above the 1.4±0.6% seen without NT-3. Therefore, NT-3 appears to marginally increase the percentage of neurons differentiating from HDRGVIII-C11.

With the immortalized rat DRG cultures, the combination of IL-11 and NGF resulted in the highest percentage (>30%) of the cells differentiating into neurons. To determine if these factors also increase the percentage of neurons in HDRG VIII-C11 cultures, HDRG VIII-C11 cells were differentiated with T, HS, Fsk, NGF plus IL-11. This resulted in 1.5±0.9% βIII-tubulin-positive neurons, similar to the percentage observed with T, HS, Fsk, G, C plus N. Thus, unlike its effect on immortalized rat DRG cells, IL-11 does not increase neuronal differentiation of the immortalized human DRG cell line HDRG VIII-C11.

Optimization of neuronal differentiation: effect of substrate. As discussed above, a higher percentage of immortalized rat DRG cells differentiated into neurons when grown on a rat tail collagen vs. polyornithine/laminin substrate. However, a comparison of the differentiation of HDRG VIII-C11 on these two substrates revealed that growth on polyornithine/laminin resulted in a marginally higher percentage (4.2±1.8%) of neurons compared to growth on rat tail collagen (2.8±1.2%). Therefore, unlike its effect on immortalized rat DRG cells, differentiation on a rat tail collagen substrate does not increase neuronal differentiation of the immortalized human DRG cell line HDRG VIII-C11.

Characterization of sensory neuronal differentiation. To study nociceptive neuronal differentiation, we examined the expression of Islet-1 and capsaicin sensitivity. In HDRGVIII-C11 cultures differentiated with T, HS, Fsk, G, C, N plus NT-3, some but not all of the neurons expressed Islet-1.

HDRGVIII-C11 cells, differentiated with T, HS, Fsk, G, C, N plus NT-3, were processed for cobalt histology to determine if the neurons were responsive to capsaicin. Approximately 30% of the cells with neuronal morphology were sensitive to capsaicin (10 $\mu$M or 100 $\mu$M), as assessed by the presence of a cobalt precipitate. No labeled cells were observed in the absence (capsaicin, and the capsaicin (10 $\mu$M)-induced labeling was reduced substantially by the addition of capsazepine (100 $\mu$M). These results indicate that approximately a third of the neurons in differentiated HDRGVIII-C11 cultures respond to capsaicin, consistent with nociceptor phenotype.

These results indicate that the cell line, HDRGVIII-C10.6 is capable of giving rise to >50% neurons. HDRGVIII-C10.6 expresses:

Islet-1 (transcription factor required for sensory neuron development)

peripherin (mature neuronal marker)

capsaicin receptors (nociceptive neuronal marker)

HDRGVIII-C11 has been identified as a new human clonal immortalized PNS cell line that differentiates into neurons. Moreover, the presence of functional capsaicin receptors establishes that HDRGVIII-C11 can differentiate into nociceptive neurons. For these cells:

v-myc was expressed in 88% of cells in the proliferative growth condition v-myc was expressed in 1.8% of cells after differentiation NT-3 may slightly increase neuronal differentiation IL-11 does not increase neuronal differentiation polyornithine/laminin (vs. rat tail collagen) may slightly increase neuronal differentiation Islet-1 (transcription factor required for sensory neuron development) is present capsaicin receptors (nociceptive neuronal marker) are present The results also demonstrate that clones HDRGVIII-C5, C7, C22 and C26 exhibit v-myc oncoprotein in the proliferative growth condition, but not to a significant extent after growth with tetracycline, establishing that these clones contain regulatable v-myc oncoprotein. Clone HDRGVIII-C22 can be differentiated into neurons.

Example 6

Detection of Transcription Factor mRNAs in Human PNS Cell Lines

This Example illustrates the use of RT-PCR to detect the presence of sensory neuron-selective transcription factors in human PNS cell lines.

The transcription factors, Brn3a and DRG11, have recently been implicated as markers for sensory neurons. The POU-domain transcription factor, Brn3a, has been detected in migrating sensory neuron precursors (Fedtsova and Turner, Mech. Devel. 53:291–304, 1995), as well as in most post-mitotic DRG neurons (Nankina et al., Nucl. Acids Res. 21:3175–3182, 1993), but is not expressed in autonomic ganglia (Fedtsova and Turner, Mech. Devel. 53:291–304, 1995). The homeodomain protein, DRG11, is specifically expressed in post-migratory sensory neurons, but not in autonomic neurons or glia (Saito et al., Mol. Cell. Neurosci. 6:280–292, 1995). The developmental expression pattern of DRG11 suggests that it is a later marker for sensory neurons than Brn3a. Based on these reports, PCR primers were designed against human Brn3a and rat DRG11, validated on human DRG tissue, and then used to examined clone HDRGVIII-C10.6.

Figure 33A:
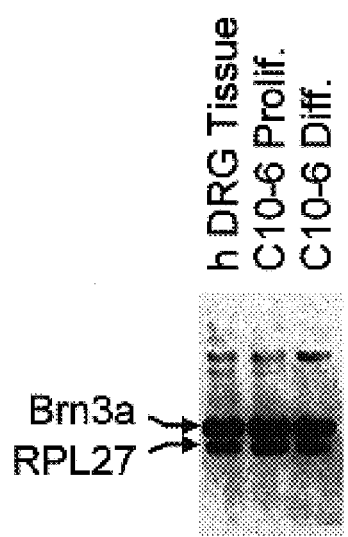
FIGS. 33A and 33B are gels depicting the results of PCR analysis of mRNA isolated from proliferative and differentiated HDRGVIII-C10.6 cells, as well as human DRG tissue, as indicated. Primers were specific for Bm3a mRNA (FIG. 33A) and DRG11 (FIG. 33B), with RPL27 as an internal control. RPL27 is a ribosomal housekeeping gene.
Figure 33B:

Brn3a mRNA was present in proliferative and differentiated HDRGVIII-C10.6 cells (FIG. 33A), consistent with clone HDRGVIII-C10.6 being of sensory neuronal lineage. Since the human DRG11 sequence has not been reported, the rat sequence was used to design primers that cross-react with the human sequence. By sequence analysis, it was determined that the human sequence amplified by these primers is 80% homologous to the rat sequence. DRG11 was clearly detected in neuronally differentiated HDRGVIII-C10.6 cells whereas only a very weak signal was present in proliferative HDRGVIII-C10.6 cells (FIG. 33B). It is possible that the weak signal detected in proliferative HDRGVIII-C10.6 cells is due to amplification of genomic DNA because the DRG11 primer set does not span an intron and a slight DNA contamination was detected in the cDNA preparation from proliferative HDRGVIII-C10.6 cells. Nevertheless, this result is consistent with the developmental expression pattern of DRG11 in the rat, and strongly suggests that clone HDRGVIII-C10.6 belongs to the sensory neuronal lineage.

The results indicate that HDRGVIII-C10.6 expressed Brn3a in both the proliferative growth condition and after neuronal differentiation, consistent with reports in the literature on the in vivo developmental expression of Brn3a. DRG11 was up-regulated after neuronal differentiation of HDRGVIII-C10.6, suggesting that these cells had differentiated into sensory neurons. Expression of the sensory neuron-selective transcription factors Brn3a and DRG11 strongly imply that clone HDRGVIII-C10.6 is derived from the sensory neuronal lineage.

The basic helix-loop-helix transcription factor, hASH-1, is the human achaete-scute homolog of MASH-1. MASH-1 is expressed transiently in the peripheral nervous system early during development, exclusively by precursors of autonomic neurons; MASH-1 is absent in cells of the sensory neuronal lineage. Therefore, the absence of hASH-1 in the human PNS lines would provide further evidence that the human PNS lines are derived from the sensory neuronal lineage. RT-PCR primers were designed and validated on the human neuroblastoma cell line, IMR-32, and then tested on proliferative and neuronally differentiated HDRGVIII-C10.6. hASH-1 was not detected to a significant extent by PCR in proliferative or neuronally differentiated HDRGVIII-C10.6, which is consistent with the derivation of HDRGVIII-C10.6 from the sensory neuronal lineage.

Example 7

Electrophysioloaical Characterization of Conditionally-immortalized Human DRG Cell Line This Example illustrates the electrophysiological properties of immortalized human DRG cell line HDRGVIII-C10.6 before and after differentiation.

The whole cell configuration of patch clamp recording was used. Seals were formed in 2 Ca— Tyrode's solution (in mM, 2 CaCl$_2$, 150 NaCl, 4 KCl, 2 MgCl$_2$, 10 glucose, 10 HEPES, pH 7.4 with NaOH) with apyrase (4 units/ml). Cells were perfused with 2 Ca-Tyrode's solution to record sodium current, or 0.5 Ca— Tyrode's to record proton-, αβ-meATP- and capsaicin-activated currents. The internal solution contained (in mM) 108 Cs— methane sulfonate, 4.5 MgCl$_2$, 9 HEPES, 9 EGTA, 4 ATP (Mg$^{2+}$ salt), 14 creatine phosphate (Tris salt) and 0.3 GTP (Tris salt) (pH 7.4 with CsOH). For eliciting sodium currents, cells were depolarized from a holding potential of −80 mV to a test potential of −10 mV. For evoking proton-, αβ-meATP- and capsaicin-activated currents, cells were held at a potential of −80 mV.

This electrophysiologicar characterization indicates that proliferating HDRGVIII-C10.6 cells do not exhibit voltage-gated sodium currents or capsaicin-activated currents. They have small α,β-meATP (100 μM) responses and small proton-gated currents (pH 5.1) (Table 3).

Figure 34:
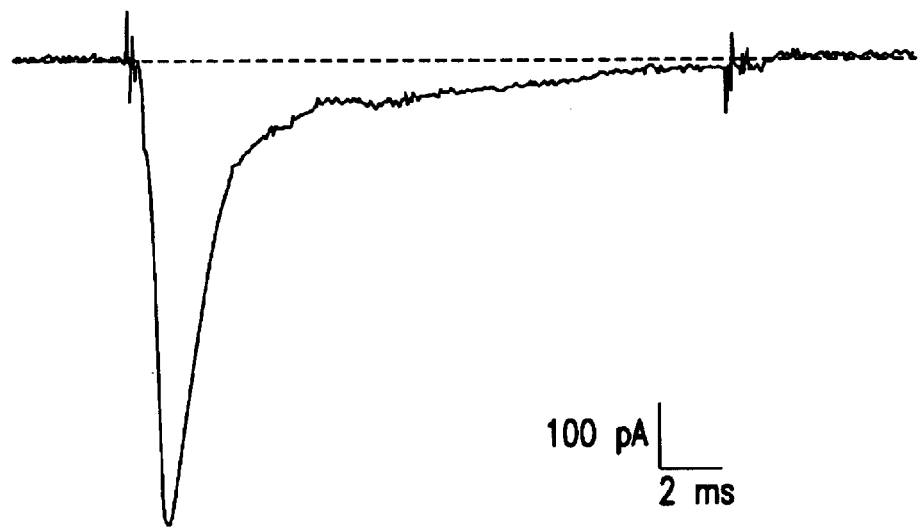
FIG. 34 depicts an electrophysiological recording of voltage-gated sodium current in a differentiated HDRGVIII-C10.6 cell.
Figure 35:
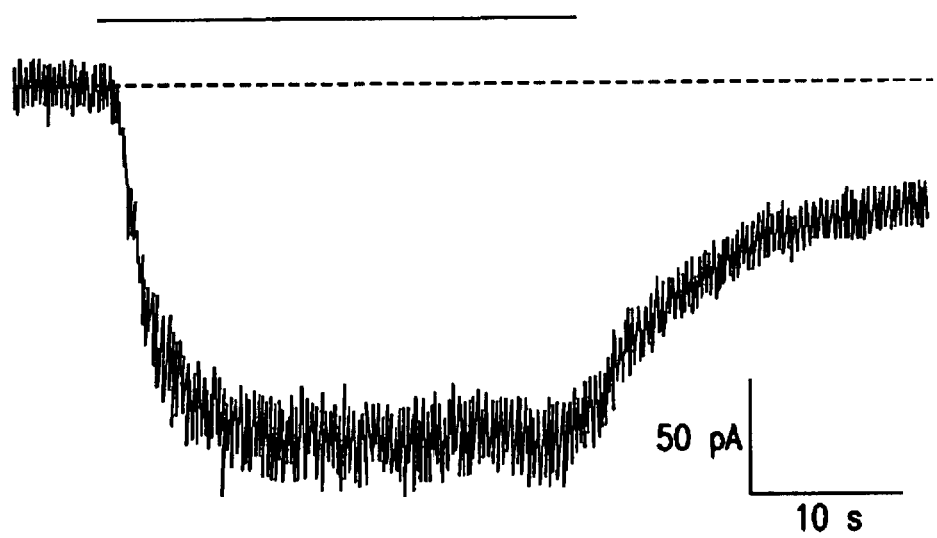
FIG. 35 depicts an electrophysiological recording of capsaicin-activated current in a differentiated HDRGVIII-C10.6 cell.
Figure 36:
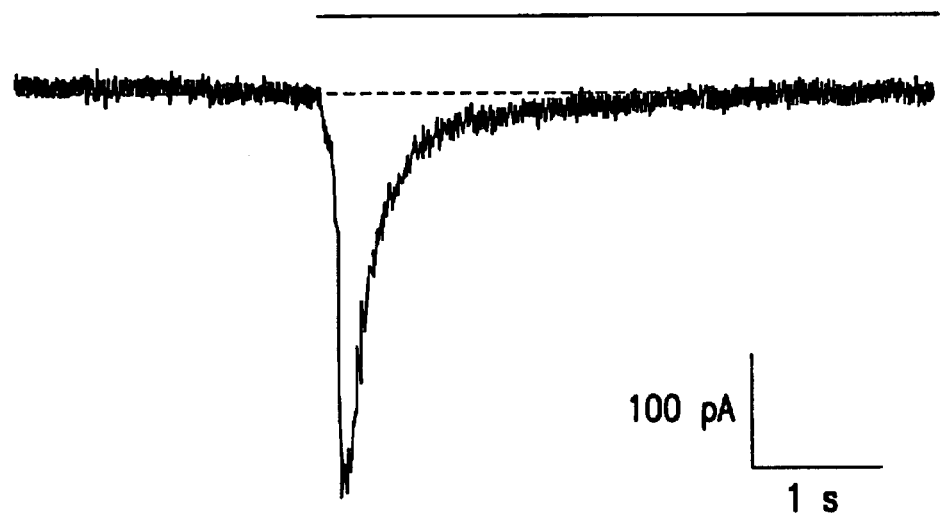
FIG. 36 depicts an electrophysiological recording of αβ-methylene-ATP-activated current in a differentiated HDRGVIII-C10.6 cell.
Figure 37:
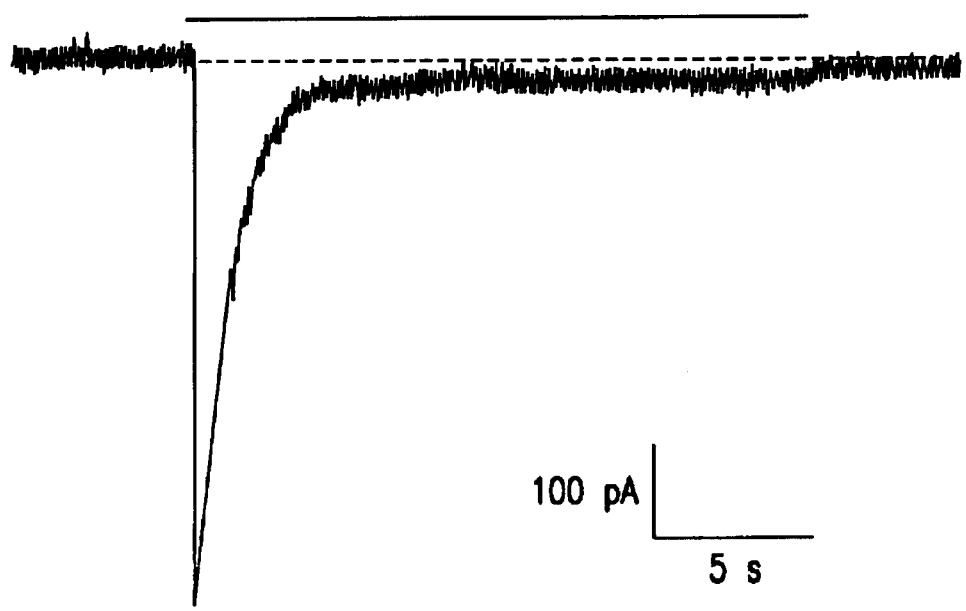
FIG. 37 depicts an electrophysiological recording of $H^+$-gated current in a differentiated HDRGVIII-C10.6 cell.

After 8–11 days of neuronal differentiation on polyornithine/laminin with tetracycline, human serum, forskolin, GDNF, CNTF plus NGF (THSFskGCN), cells with neuronal morphology expressed TTX-sensitive voltage-gated sodium currents (FIG. 34, Table 3), capsaicin (1 μM)-activated currents (FIG. 35, Table 3), αβ-meATP (100 μM)-activated currents (FIG. 36, Table 3) and proton-gated currents (FIG. 37, Table 3, pH 5.1).

TABLE 3

Electrophysiological Characterization of HDRGVIII-C10.6

| Growth Condition | Diff'n. Length (days) | I (pA) | | | | |
|---|---|---|---|---|---|---|
| | | Sodium | Purinergic (αβmeATP) | Proton Total | Sustained | Capsaicin |
| Proliferative | | 0 (n = 5) | 29 ± 15 (n = 3) | 251 ± 40 (n = 4) | 24 ± 15 (n = 4) | 0 (n = 3) |
| THSFskGCN | 8 | 165 ± 70 (n = 4) | 3 ± 3 (n = 2) | 615 (n = 1) | 45 (n = 1) | 114 ± 14 (n = 4) |
| THSFskGCN | 11 | 798 ± 186 (n = 8) | 226 ± 80 (n = 4) | 427 ± 206 (n = 4) | 15 ± 11 (n = 4) | 217 ± 36 (n = 4) |

The results indicate that differentiation of HDRGVIII-C10.6 is required for expression of functional voltage- and ligand-gated currents. After differentiation, HDRGVIII-C10.6 cells with neuronal morphology exhibit the following functional currents:

TTX-sensitive voltage-gated sodium currents (consistent with neuronal phenotype)

capsaicin-activated currents (consistent with nociceptive sensory neuronal phenotype)

α,β-meATP-activated currents (consistent with sensory neuronal phenotype)

proton-gated currents (consistent with sensory neuronal phenotype)

From the foregoing, it will be appreciated that, although specific embodiments of the invention have been described herein for the purpose of illustration, various modifications may be made without deviating from the spirit and scope of the invention.

What is claimed is:

1. A method for producing a conditionally-immortalized dorsal root ganglion progenitor cell, comprising:
    (a) transfecting dorsal root ganglion progenitor cells plated on a first surface and in a first growth medium that permit proliferation with DNA encoding a selectable marker and a regulatable oncogene; and
    (b) passaging the transfected cells onto a second surface and in a second growth medium that permit attachment and proliferation; and therefrom producing a conditionally-immortalized dorsal root ganglion progenitor cell.

2. A method according to claim 1, wherein the dorsal root ganglion progenitor cells are rat cells.

3. A method according to claim 1, wherein the dorsal root ganglion progenitor cells are human cells.

4. A method according to claim 1 wherein the first and second surfaces are independently selected, and wherein the first and second surfaces comprise one or more substrates selected from the group consisting of a polyamino acid, fibronectin, laminin, collagen and tissue culture plastic.

5. The method of claim 1 wherein the oncogene encodes a protein selected from the group consisting of v-myc, N-myc, c-myc, SV40 large T antigen, polyoma large T antigen, E1a protein of adenovirus, and E7 protein of human papillomavirus.

6. The method of claim 5 wherein the oncogene is v-myc.

7. A conditionally-immortalized dorsal root ganglion progenitor cell containing an oncogene, wherein the cell differentiates into neurons upon inhibition of the expression of the oncogene.

8. A cell according to claim 7, wherein the cell is a rat dorsal root ganglion progenitor cell transfected with an oncogene.

9. A cell according to claim 7, wherein the cell is a human dorsal root ganglion progenitor cell transfected with an oncogene.

10. A cell according to claim 7, wherein the cell differentiates into sensory neurons under appropriate culture conditions.

11. A cell according to claim 7, wherein the cell differentiates into nociceptive sensory neurons under appropriate culture conditions.

12. A method for producing neurons, comprising culturing a cell produced according to claim 1 under conditions inhibiting expression of the regulatable oncogene.

13. A method according to claim 12, wherein the cells are conditionally-immortalized rat or human dorsal root ganglion progenitor cells, and wherein the cells are cultured on a substrate in the presence of one or more differentiating agents.

14. A method for producing neurons, comprising culturing a conditionally-immortalized dorsal root ganglion progenitor cell containing an oncogene under conditions inhibiting expression of the oncogene, wherein said cell differentiates into neurons upon inhibition of the expression of the oncogene.

15. A method according to claim 14, wherein said cell is a conditionally-immortalized rat or human dorsal root ganglion progenitor cell, and wherein said cell is cultured in the presence of one or more differentiating agents.

16. A method for determining whether or not a conditionally-immortalized dorsal root ganglion progenitor cell is capable of differentiation into a neuron, comprising the steps of:
   (a) detecting the presence or absence of β-III-tubulin expression in the cell in the proliferative growth condition; and
   (b) if β-III-tubulin expression is detected, identifying said cell expressing β-III-tubulin as a conditionally-immortalized dorsal root ganglion progenitor cell that differentiates into neurons under cell culture conditions that allow conditionally-immortalized precursor cells to differentiate into neurons.

17. A method of identifying an agent that modulates the level or activity of a protein produced by a dorsal root ganglion progenitor cell, comprising:
   (a) contacting a cell produced according to the method of claim 1 with a candidate agent;
   (b) determining the level or activity of said protein in the presence of said agent and in the absence of said agent; and
   (c) comparing the level or activity of said protein in the presence of said agent with the level or activity of said protein in the absence of said agent,
wherein if said level or activity of said protein in the presence of said agent is different than the level or activity of said protein in the absence of said agent, said agent is identified as an agent that modulates the level or activity of a protein produced by a dorsal root ganglion progenitor cell.

18. A method for identifying an agent that modulates the level or activity of a protein produced by a dorsal root ganglion progenitor cell, comprising:
   (a) contacting a cell according to claim 7 with a candidate agent;
   (b) determining the level or activity of said protein in the presence of said agent and in the absence of said agent; and
   (c) comparing the level or activity of said protein in the presence of said agent with the level or activity of said protein in the absence of said agent,
wherein if said level or activity of said protein in the presence of said agent is different than the level or activity of said protein in the absence of said agent, said agent is identified as an agent that modulates the level or activity of a protein produced by a dorsal root ganglion progenitor cell.

19. A method for detecting the presence or absence of a protein in a sample, comprising:
   (a) contacting a sample with a cell produced according to the method of claim 1; and
   (b) subsequently detecting a response or lack of response in the cell,
wherein said response indicates the presence of said protein and said lack of response indicates the absence of the protein, and wherein said response is selected from the group consisting of a change in the level of an mRNA in said cell, a change in the level of a protein in said cell, and a change in the activity of a protein in said cell.

20. A method for detecting the presence or absence of a protein in a sample, comprising:
   (a) contacting a sample with a cell according to claim 7; and
   (b) subsequently detecting a response or lack of response in the cell,
wherein said response indicates the presence of said protein and said lack of response indicates the absence of the protein, and wherein said response is selected from the group consisting of a change in the level of an mRNA in said cell, a change in the level of a protein in said cell, and a change in the activity of a protein in said cell.

21. A method of detecting a human dorsal root ganglion nucleic acid or protein, comprising detecting the presence of said nucleic acid or protein within a cell produced according to the method of claim 1.

22. A method of detecting a human dorsal root ganglion nucleic acid or protein, comprising detecting the presence of said nucleic acid or protein within a cell according to claim 7.

23. A method of identifying an agent that affects dorsal root ganglion progenitor cell death, comprising:
   (a) contacting a plurality of cells produced according to the method of claim 1 with a candidate agent under conditions that, in the absence of the candidate agent, result in death of said plurality of cells;
   (b) determining the number of said plurality of cells that die in the presence of said agent; and
   (c) comparing the number of said plurality of cells that die in the presence of said agent to the number of said plurality of cells that die in the absence of said agent,
wherein if the number of said plurality of cells that die in the presence of said agent is different than said number of said plurality of cells that die in the absence of said agent, said agent is identified as an agent that affects dorsal root ganglion progenitor cell death.

24. A method for screening for an agent that affects dorsal root ganglion progenitor cell death, comprising:
   (a) contacting a plurality of cells according to claim 7 with a candidate agent under conditions that, in the absence of the candidate agent, result in death of said plurality of cells; and
   (b) determining the number of said plurality of cells that die in the presence of said agent; and
   (c) comparing the number of said plurality of cells that die in the presence of said agent to the number of said plurality of cells that die in the absence of said agent,
wherein if said number of said plurality of cells that die in the presence of said agent is different than said number of said plurality of cells that die in the absence of said agent, said agent is identified as an agent that affects dorsal root ganglion progenitor cell death.

25. A method for screening for a protein that regulates dorsal root ganglion progenitor cell death, comprising:
   (a) altering the level of expression of a protein within a plurality of cells produced according to the method of claim 1;
   (b) determining the number of said plurality of cells that die when said level of expression of said protein is altered and when said level of expression is not altered; and
   (c) comparing the number of said plurality of cells that die when said level of expression is altered to the number of said plurality of cells that die when said level of expression is not altered,
wherein if said number of said plurality of cells that die when said level of expression is altered is different than said number of said plurality of cells that die when said level of expression is not altered, said agent is identified as an agent that affects dorsal root ganglion progenitor cell death.

26. A method for screening for a protein that regulates dorsal root ganglion progenitor cell death, comprising:

(a) altering the level of expression of a protein within a plurality of cells according to claim 7;

(b) determining the number of said plurality of cells that die when said level of expression of said protein is altered and when said level of expression is not altered; and (c) comparing the number of said plurality of cells that die when said level of expression is altered to the number of said plurality of cells that die when said level of expression is not altered, wherein if said number of said plurality of cells that die when said level of expression is altered is different than said number of said plurality of cells that die when said level of expression is not altered, said agent is identified as an agent that affects dorsal root ganglion progenitor cell death.

27. A method for identifying an agent that modulates the level or activity of a protein produced by a dorsal root ganglion neuron, comprising:

(a) contacting a cell produced according to the method of claim 12 with a candidate agent;

(b) determining the level or activity of said protein in the presence and absence of said agent; and (c) comparing the level or activity of said protein in the presence of said agent with the level or activity of said protein in the absence of said agent, wherein if said level or activity of said protein in the presence of said agent is different than the level or activity of said protein in the absence of said agent, said agent is identified as an agent that modulates the level or activity of a protein produced by a dorsal root ganglion neuron.

28. A method for detecting the presence or absence of a protein in a sample, comprising:

(a) contacting a sample with a cell produced according to the method of claim 12; and (b) subsequently detecting a response or lack of response in the cell, wherein a response indicates the presence of said protein and said lack of response indicates the absence of the protein, and wherein said response is selected from the group consisting of a change in the level of an mRNA in said cell, a change in the level of a protein in said cell, and a change in the activity of a protein in said cell.

29. A method of detecting a human dorsal root ganglion gene or protein, comprising detecting the presence of a gene or protein within a culture of cells produced according to the method of claim 12.

30. A method for screening for an agent that affects dorsal root ganglion neuronal cell death, comprising:

(a) contacting a plurality of cells according to the method of claim 12 with a candidate agent under conditions that, in the absence of the candidate agent, result in death of said plurality of cells;

(b) determining the number of said plurality of cells that die in the presence of said agent; and (c) comparing the number of said plurality of cells that die in the presence of said agent to the number of said plurality of cells that die in the absence of said agent, wherein if said number of said plurality of cells that die in the presence of said agent is different than said number of said plurality of cells that die in the absence of said agent, said agent is identified as an agent that affects dorsal root ganglion neuronal cell death.

31. A method for screening for a protein that regulates dorsal root ganglion neuronal cell death, comprising:

(a) altering the level of expression of a protein within a plurality of cells produced according to the method of claim 12;

(b) determining a number of said plurality of cells that die when said level of expression of said protein is altered and when said level of expression is not altered; and (c) comparing the number of said plurality of cells that die when said level of expression is altered to the number of said plurality of cells that die when said level of expression is not altered, wherein if said number of said plurality of cells that die when said level of expression is altered is different than said number of said plurality of cells that die when said level of expression is not altered, said agent is identified as an agent that affects dorsal root ganglion neuronal cell death.

* * * * *